US011738008B2

(12) United States Patent
Liotta et al.

(10) Patent No.: US 11,738,008 B2
(45) Date of Patent: Aug. 29, 2023

(54) N-METHYL-D-ASPARTIC ACID RECEPTOR MODULATORS

(71) Applicant: Emory University, Atlanta, GA (US)

(72) Inventors: Dennis Liotta, Atlanta, GA (US); Stephen F. Traynelis, Atlanta, GA (US); David Menaldino, Atlanta, GA (US); Matthew Epplin, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 16/968,114

(22) PCT Filed: Feb. 9, 2019

(86) PCT No.: PCT/US2019/016779

§ 371 (c)(1),
(2) Date: Aug. 6, 2020

(87) PCT Pub. No.: WO2019/157014

PCT Pub. Date: Aug. 15, 2019

(65) Prior Publication Data

US 2021/0361631 A1 Nov. 25, 2021

Related U.S. Application Data

(60) Provisional application No. 62/626,921, filed on Feb. 6, 2018.

(51) Int. Cl.

| | |
|---|---|
| ***C07D 495/04*** | (2006.01) |
| ***A61K 31/4365*** | (2006.01) |
| ***A61K 31/4355*** | (2006.01) |
| ***A61K 31/437*** | (2006.01) |
| ***A61K 31/4985*** | (2006.01) |
| ***C07D 471/04*** | (2006.01) |
| ***C07D 487/04*** | (2006.01) |
| ***C07D 491/048*** | (2006.01) |
| ***C07D 513/04*** | (2006.01) |

(52) U.S. Cl.

CPC ........ *A61K 31/4365* (2013.01); *A61K 31/437* (2013.01); *A61K 31/4355* (2013.01); *A61K 31/4985* (2013.01); *C07D 471/04* (2013.01); *C07D 487/04* (2013.01); *C07D 491/048* (2013.01); *C07D 495/04* (2013.01); *C07D 513/04* (2013.01)

(58) Field of Classification Search

CPC ............. C07D 495/04; C07D 491/048; C07D 487/04; C07D 513/04; C07D 471/04; C07D 498/04; A61K 31/436; A61K 31/4365; A61K 31/437; A61K 31/4985; A61K 31/4355

USPC ...... 544/105, 349, 350; 546/112; 514/230.5, 514/249, 250, 301, 302, 303, 350

See application file for complete search history.

(56) References Cited

U.S. PATENT DOCUMENTS

| | | | |
|---|---|---|---|
| 8,420,680 | B2 | 4/2013 | Liotta |
| 8,822,462 | B2 | 9/2014 | Traynelis |
| 9,079,852 | B2 | 7/2015 | Liotta |
| 10,273,214 | B2 | 4/2019 | Traynelis |
| 10,647,679 | B2 | 5/2020 | Strong |
| 2010/0222332 | A1 | 9/2010 | Lavergne |
| 2011/0105514 | A1 | 5/2011 | Aissaoui |

FOREIGN PATENT DOCUMENTS

| | | |
|---|---|---|
| WO | 2016149248 | 9/2016 |

OTHER PUBLICATIONS

Bliss et al., A synaptic model of memory: long-term potentiation in the hippocampus. Nature 1993, 361, 31-39.

Brossi et al. Synthesen in der Isochinolinreihe Halogensubstituierte 1-(ω-Phenylalkyl)-1,2,3,4-tetrahydro-isochinolineals Analgetica, HCA, 1960, 43(6):1459-1472.

Collingridge et al., The NMDA receptor as a target for cognitive enhancement. Neuropharmacology 2013, 64, 13-26.

Dravid et al., Activation of recombinant NR1/NR2C NMDA receptors. J. Physiol. 2008, 586, 4425-4439.

Epplin et al., Discovery of dihydropyrrolo[1,2-a]pyrazin-3(4H)-one-based second-generation GluN2C- and GluN2D-selective positive allosteric modulators (PAMs) of the N-methyl-D-aspartate (NMDA) receptor. J. Med. Chem. 2020, 63, 7569-7600.

(Continued)

*Primary Examiner* — Jeffrey H Murray

(74) *Attorney, Agent, or Firm* — Emory Patent Group

(57) ABSTRACT

A series of subunit selective allosteric modulators of NMDA receptor function according to Formula (I) is provided herein. Also provided is a method of treating neurological disorders such as Alzheimer's disease Parkinson's disease, schizophrenia, depression, stroke, psychosis and the like using compounds of Formula (I), optionally in combination with one or more further active agent. Pharmaceutical compositions containing a compound of Formula (I) and optionally one or more active agent for treating such disorders may be provided in the form of a tablet, capsule, pill, gel, granules, aerosol, aqueous buffer or a nanoparticle formulation, emulsion, liposome, etc. (I)

Formula (I)

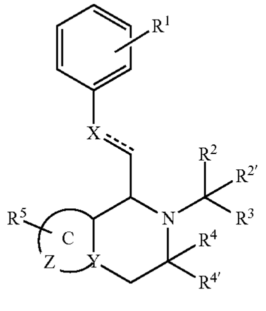

9 Claims, No Drawings

(56) References Cited

OTHER PUBLICATIONS

Erreger et al., Subunit-specific agonist activity at NR2A-, NR2B-, NR2C-, and NR2D-containing N-methyl-D-aspartate glutamate receptors. Mol. Pharmacol. 2007, 72, 907-920.
Freel et al., Synthesis and structure activity relationship of tetrahydroisoquinoline-based potentiators of GluN2C and GluN2D containing N-methyl-D-aspartate receptors. J. Med. Chem. 2013, 56, 5351-5381.
Hughes et al., Cellular and synaptic mechanisms of anti-NMDA receptor encephalitis. J. Neurosci. 2010, 30, 5866-5875.
Karakas et al., Crystal structure of a heterotetrameric NMDA receptor ion channel. Science 2014, 344 (6187), 992-997.
Kemp et al., NMDA receptor pathways as drug targets. Nat. Neurosci. 2002, 5, 1039-1042.
Lipton, Failures and successes of NMDA receptor antagonists: molecular basis for the use of open-channel blockers like memantine in the treatment of acute and chronic neurologic insults. NeuroRx 2004, 1, 101-110.
Moghaddam, From revolution to evolution: the glutamate hypothesis of schizophrenia and its implication for treatment. Neuropsychopharmacology 2012, 37, 4-15.
Monyer et al., Developmental and regional expression in the rat brain and functional properties of four NMDA receptors. Neuron 1994, 12, 529-540.
Mullasseril et al., A subunit-selective potentiator of NR2C- and NR2D-containing NMDA receptors. Nat. Commun. 2010, 1, 90.
Ogden et al., Potentiation of GluN2C/D NMDA receptor subtypes in the amygdala facilitates the retention of fear and extinction learning in mice. Neuropsychopharmacology 2014, 39, 625-637.
Okabe et al., Hippocampal synaptic Plasticity in mice overexpressing an embryonic subunit of the NMDA receptor. J. Neurosci. 1998, 18, 4177-4188.
Paoletti et al., NMDA receptor subunit diversity: impact on receptor properties, synaptic plasticity and disease. Nature Reviews 2013, 13, 383-400.
Reisberg et al., Memantine in moderate-to-severe Alzheimer's disease. N. Engl. J. Med. 2003, 348, 1333-1341.
Schmeisser et al., Autistic-like behaviours and hyperactivity in mice lacking ProSAP1/Shank2. Nature 2012, 486, 256-260.
Strong et al., The structure-activity relationship of a tetrahydroisoquinoline class of N-methyl-D-aspartate receptor modulators that potentiates GluN2B-containing N-methyl-D-aspartate receptors. J. Med. Chem. 2017, 60, 5556-5585.
Suryavanshi et al., GluN2C/GluN2D subunit-selective NMDA receptor potentiator CIQ reverses MK-801-induced impairment in prepulse inhibition and working memory in Y-maze test in mice. Br J. Pharmacol. 2014, 171, 799-809.
Tang et al., Genetic enhancement of learning and memory in mice. Nature 1999, 401, 63-69.
Traynelis et al., Glutamate receptor ion channels: structure, regulation, and function. Pharmacol. Rev. 2010, 62, 405-496.
Vance et al., GluN1 splice variant control of GluN1/GluN2D NMDA receptors. J. Physiol. 2012, 590, 3857-3875.
Won et al., Autistic-like social behaviour in Shank2-mutant mice improved by restoring NMDA receptor function. Nature 2012, 486, 261-265.

N-METHYL-D-ASPARTIC ACID RECEPTOR MODULATORS

CROSS REFERENCE TO RELATED APPLICATIONS

This application is the National Stage of International Application No. PCT/US2019/016779, which claims the benefit of U.S. Provisional Application No. 62/626,921 filed Feb. 6, 2018. The entirety of each of these applications is hereby incorporated by reference for all purposes.

STATEMENT REGARDING FEDERALLY FUNDED RESEARCH

This invention was made with government support under NS065371 awarded by the National Institutes of Health. The government has certain rights in the invention.

TECHNICAL FIELD

The present disclosure relates to N-methyl-D-aspartic acid receptor (NMDAR) modulators and, in particular, to subunit specific allosteric modulators of NMDARs for the treatment of neurological disorders, such as Alzheimer's disease, Parkinson's disease, schizophrenia, depression, stroke, psychosis and the like. It also relates to pharmaceutical compositions and methods of treatment of such neurological disorders.

BACKGROUND

NMDA receptors belong to the family of ionotropic glutamate receptors alongside the 2-amino-3-(5-methyl-3-oxo-1,2-oxazol-4-yl)propanoic acid receptors (AMPARs) and kainic acid receptors and are expressed extensively throughout the central nervous system (CNS). (Traynelis et al., Glutamate receptor ion channels: structure, regulation, and function. *Pharmacol. Rev.* 2010, 62, 405-496.)

Each NMDAR assembles as a tetrameric heterodimer consisting of two obligatory GluN1 subunits and two GluN2 subunits. Opening of the cation-selective pore is induced via binding of co-agonists glycine and glutamate to the GluN1 and GluN2 subunits, respectively. Upon co-agonist binding and membrane depolarization to remove $Mg^{2+}$ block, (Nowak et al., Magnesium gates glutamate-activated channels in mouse central neurones. *Nature* 1984, 307, 462-465; Mayer et al., Voltage-dependent block by $Mg^{2+}$ of NMDA responses in spinal cord neurones. *Nature* 1984, 309, 261-263), $Ca^{2+}$ and $Na^{+}$ ions flow into the cell contributing to post-synaptic signal transmission (MacDermott et al., NMDA-receptor activation increases cytoplasmic calcium concentration in cultured spinal cord neurones. *Nature,* 1986, 321, 519-522). Four isoforms of the GluN2 subunit (GluN2A, GluN2B, GluN2C and GluN2D) are expressed with different spatiotemporal patterns in the brain (Monyer et al., Developmental and regional expression in the rat brain and functional properties of four NMDA receptors. *Neuron* 1994, 12, 529-540; Akazawa et al., Differential expression of five N-methyl-D-aspartate receptor subunit mRNAs in the cerebellum of developing and adult rats. *J. Comp. Neurol.* 1994, 347, 150-160; Watanabe et al., Developmental changes in distribution of NMDA receptor channel subunit mRNAs. *NeuroReport* 1992, 3, 1138-1140; Karakas et al., Crystal structure of a heterotetrameric NMDA receptor ion channel. *Science* 2014, 344 (6187), 992-997) and endow the receptor with unique pharmacological properties including open probability (Erreger et al., Subunit-specific gating controls rat NR1/NR2A and NR1/NR2B NMDA channel kinetics and synaptic signaling profiles. *J. Physiol.* 2005, 563, 345-358; Dravid et al., Activation of recombinant NR1/NR2C NMDA receptors. *J. Physiol.* 2008, 586, 4425-4439; Wyllie et al., Single-channel activations and concentration jumps: comparison of recombinant NR1a/NR2A and NR1a/NR2D NMDA receptors. *J. Physiol.* 1998, 510, 1-18; Vance et al., GluN1 splice variant control of GluN1/GluN2D NMDA receptors. *J.* Physiol. 2012, 590, 3857-3875), agonist potency (Erreger et al., Subunit-specific agonist activity at NR2A-, NR2B-, NR2C-, and NR2D-containing N-methyl-D-aspartate glutamate receptors. *Mol. Pharmacol.* 2007, 72, 907-920), and deactivation time course (Vicini et al., Functional and pharmacological differences between recombinant N-methyl-D-aspartate receptors. *J. Neurophysiol.* 1998, 79, 555-566).

NMDARs play a role in neurological functions including memory, learning, (Tang et al., Genetic enhancement of learning and memory in mice. Nature 1999, 401, 63-69; Collingridge et al., The NMDA receptor as a target for cognitive enhancement. *Neuropharmacology* 2013, 64, 13-26) and synaptic plasticity (Okabe et al., Hippocampal synaptic Plasticity in mice overexpressing an embryonic subunit of the NMDA receptor. *J. Neurosci.* 1998, 18, 4177-4188; Bliss et al., A synaptic model of memory: long-term potentiation in the hippocampus. *Nature* 1993, 361, 31-39) and have long been connected to basic neurological function. They have been implicated in a wide range of neurological diseases and disorders. Both hypo- and hyper-function of NMDARs has been connected to Alzheimer's disease, Parkinson's disease, schizophrenia, depression, stroke, and psychosis, among others (Paoletti et al., NMDA receptor subunit diversity: impact on receptor properties, synaptic plasticity and disease. *Nature Reviews* 2013, 13, 383-400; Traynelis et al., Glutamate receptor ion channels: structure, regulation, and function. *Pharmacol. Rev.* 2010, 62 (3), 405-496; and Kemp et al., NMDA receptor pathways as drug targets. *Nat. Neurosci.* 2002, 5, 1039-1042). There has thus been significant interest in developing NMDAR PAMs as reduced NMDAR activity has been implicated in schizophrenia (Moghaddam, From revolution to evolution: the glutamate hypothesis of schizophrenia and its implication for treatment. *Neuropsychopharmacology* 2012, 37, 4-15), autism (Won et al., Autistic-like social behaviour in Shank2-mutant mice improved by restoring NMDA receptor function. *Nature* 2012, 486, 261-265; Schmeisser et al., Autistic-like behaviours and hyperactivity in mice lacking ProSAP1/Shank2. *Nature* 2012, 486, 256-260), encephalitis (Hughes et al., Cellular and synaptic mechanisms of anti-NMDA receptor encephalitis. *J. Neurosci.* 2010, 30, 5866-5875) and age-related memory loss (Paoletti et al., NMDA receptor subunit diversity: impact on receptor properties, synaptic plasticity and disease. *Nat. Rev. Neurosi.* 2013, 14, 383-400).

Previous FDA approved drugs that target NMDARs, e.g. memantine for moderate-to-severe Alzheimer's disease (Reisberg et al., Memantine in moderate-to-severe Alzheimer's disease. *N. Engl. J. Med.* 2003, 348, 1333-1341), non-selectively block the well-conserved ion pore irrespective of subunit composition leading to extensive neurological side effects. Recently, subunit-selective modulators of the receptor have been the focus of the community to potentially reduce the side effect profile (Lipton, Failures and successes of NMDA receptor antagonists: molecular basis for the use of open-channel blockers like memantine in the treatment of acute and chronic neurologic insults. *Neu-*

*roRx* 2004, 1, 101-110) while maintaining the ability to alleviate receptor dysfunction and ultimately provide treatment for these conditions.

A tetrahydroisoquinoline series of PAMs typified by CIQ (see below), selective for the GluN2C/D subunits and showing no activity at GluN2A/B, AMPAR, or kainate receptors has been previously described (Mullasseril et al., A subunit-selective potentiator of NR2C- and NR2D-containing NMDA receptors. *Nat. Commun.* 2010, 1, 90; Santangelo Freel et al., Synthesis and structure activity relationship of tetrahydroisoquinoline-based potentiators of GluN2C and GluN2D containing N-methyl-D-aspartate receptors. *J. Med. Chem.* 2013, 56, 5351-5381).

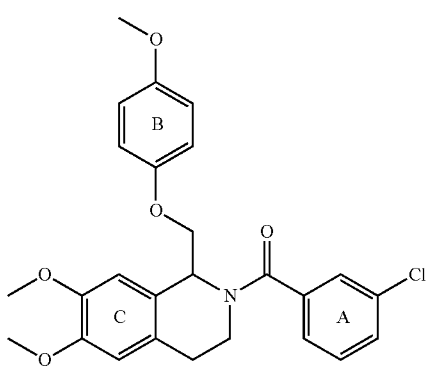

CIQ

Specifically, CIQ has been shown to attenuate schizophrenia-like symptoms (Suryavanshi et al., GluN2C/GluN2D subunit-selective NMDA receptor potentiator CIQ reverses MK-801-induced impairment in prepulse inhibition and working memory in Y-maze test in mice. *Br. J. Pharmacol.* 2014, 171, 799-809) and facilitate the retention of fear and extinction learning (Ogden et al., Potentiation of GluN2C/D NMDA receptor subtypes in the amygdala facilitates the retention of fear and extinction learning in mice. *Neuropsychopharmacology* 2014, 39, 625-637) in animal models emphasizing the clinical potential of a potent, GluN2C/D selective PAM. However, despite CIQ's use as a tool compound, there are still significant problems with the scaffold that must be overcome before a clinical lead is produced. First and foremost is the modest potency, between 5-10 μM at GluN2C/D with 2-fold potentiation for CIQ (Mullasseril et al., A subunit-selective potentiator of NR2C- and NR2D-containing NMDA receptors. *Nat. Commun.* 2010, 1, 90). A large synthetic effort resulted in a >10-fold improvement in potency to 0.3 μM, but came largely at the expense of druggable properties. These potency improvements required additions of large lipophilic substituents to a scaffold that already suffers from poor aqueous solubility, highlighting the second major obstacle of the scaffold (Santangelo Freel et al., Synthesis and structure activity relationship of tetrahydroisoquinoline-based potentiators of GluN2C and GluN2D containing N-methyl-D-aspartate receptors. *J. Med. Chem.* 2013, 56, 5351-5381). This is only further backed by the high A Log P values (>5) of CIQ and its derivatives, providing ominous prospects for its oral availability in the clinic and limiting its usefulness as a tool compound. Also see, U.S. Pat. Nos. 8,822,462, 9,079,852 and PCT application No. WO 2016/149248.

There is thus a need for NMDA receptor modulators that alleviate some of the abovementioned problems, at least to some extent.

SUMMARY

This disclosure covers a series of subunit selective allosteric modulators of NMDA receptor function.

According to one embodiment of the present disclosure, there is provided a compound of Formula (I), or salts thereof, Formula (I)

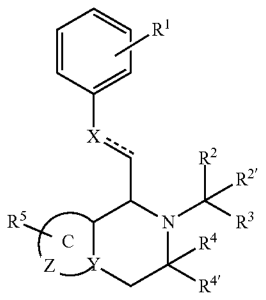

wherein $R^1$ is selected from H, alkyl, alkoxy, aryl and heteroaryl, halogen, hydroxy, amide, amine, alkylamino, aminoalkyl, nitrile, nitro or $OCF_3$;

$R^2$ and $R^{2'}$ are each, individually H, or together form a ═O, ═S, or ═NH;

$R^3$ is an alkyl, alkoxy, aryl or heteroaryl ring, wherein $R_3$ is optionally substituted with $R^5$;

$R^4$ and $R^{4'}$ are each, individually H, or together form a ═O, ═S, or ═NH;

Ring C is a five membered aryl or a five or six membered heteroaryl or heterocyclyl ring; and $R^5$ is an H, alkyl, aryl, heteroaryl, carbocyclyl, heterocarbocyclyl, alkoxy, amine, amide, halogen, hydroxy, nitrile, nitro, or $CF_3$;

X is O, CH, $CH_2$ or NH;

Y is N or $CH_2$; and

Z is CH, $CH_2$, N, NH, S or O; and

The dashed bond represented by ---, is either a single bond or a double bond.

In further features of this embodiment, $R^1$ is selected from H, OH, Me, OMe, Et, OEt, Pr, OPr, Bu, OBu, Pent, or OPent, Hex, OHex each of which may be saturated, unsaturated, straight or branched, OBn, Ph, Cl, Br, F, I, CN, $NH_2$, NHMe, $NMe_2$, NHEt, $NEt_2$, NMeiPr, $NiPr_2$, $NO_2$, $OCF_3$, aryl or heteroaryl, N-morpholine, N-piperidine;

$R^2$ and $R^{2'}$ are each, individually H, or together form a ═O, ═S, or ═NH;

$R^3$ is selected from an H, Me, OH, OMe, Et, OEt, Pr, OPr, Bu, OBu, Pent, or OPent, each of which may be saturated, unsaturated, straight or branched, OBn, Ph, Cl, Br, F, I, CN, $NH_2$, NHMe, $NMe_2$, NHEt, $NEt_2$, $NO_2$, $OCF_3$ or a heteroaryl, wherein $R_3$ is optionally substituted with $R^5$;

$R^4$ and $R^{4'}$ are each, individually H, or together form a ═O, ═S, or ═NH;

Ring C is a thiophene, thiazole, isothiazole, pyrrole, pyrazole, furan, tetrahydrothiophene, isothiazolidine, thiazolidine, pyrrolidine, pyrazolidine, tetrahydrofuran, pyridine, pyrazine, triazine, piperidine, tetrahydropyran, morpholine, or piperazine; and $R^5$ is an H, Me, OH, OMe, Et, OEt, Pr, OPr, Bu, OBu, Pent, or OPent, each of which may be saturated, unsaturated, straight or branched, OBn, Ph, Cl, Br, F, I, CN, $NH_2$, NHMe, $NMe_2$, NHEt, $NEt_2$, $NO_2$, $OCF_3$, $OCH(CH_2CH_3)_2$, aryl or heteroaryl, N-morpholine, N-piperidine;

X is O or CH, or $CH_2$; and the dashed bond, represented by , is either a single bond or a double bond.

The compounds of Formula (I) may be selected from compounds of Formula (IA), (IB), (IC) or (ID) or salts thereof, Formula (IA)

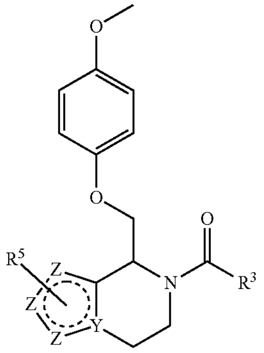

Formula (IB)

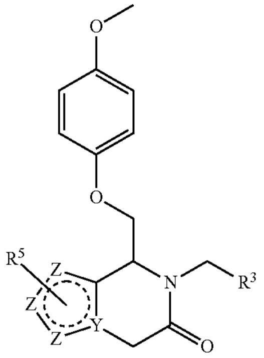

Formula (IC)

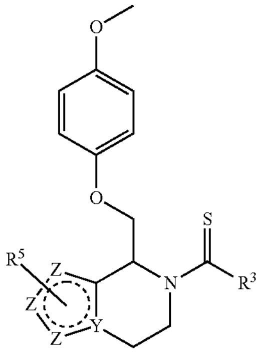

-continued (Formula ID)

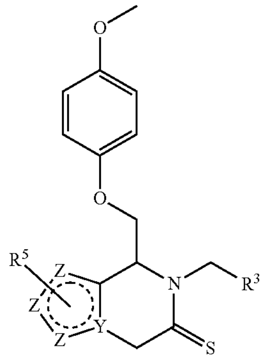

wherein $R^3$, $R^5$, Y and Z are as defined above and the dashed circle with the five membered ring, represented as , indicates that the ring may be saturated or unsaturated.

The compounds of Formula (I) may be selected from compounds of Formula (IE), (IF), (IG) or (IH) or salts thereof, Formula (IE)

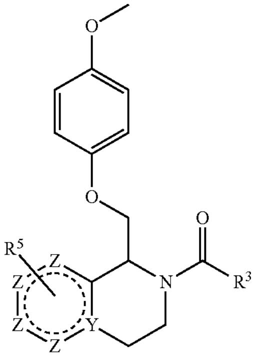

Formula (IF)

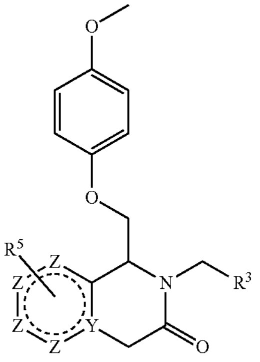

-continued
Formula (IH)
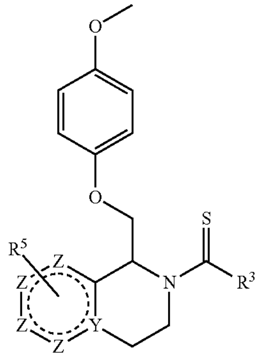
Formula (IG)
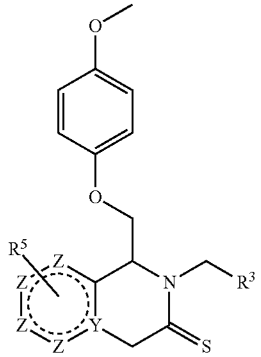
wherein $R^3$, $R^5$, Y and Z are as defined above and at least either one Z or Y is not CH or $CH_2$ and the dashed circle with the six membered ring, represented as , indicates that the ring may be saturated or unsaturated.
In a preferred embodiment, the compounds are selected from:
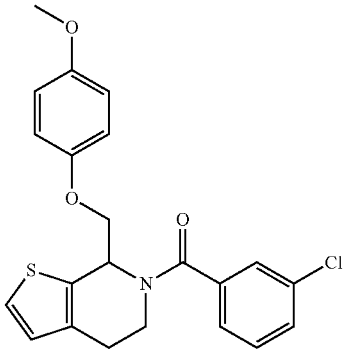
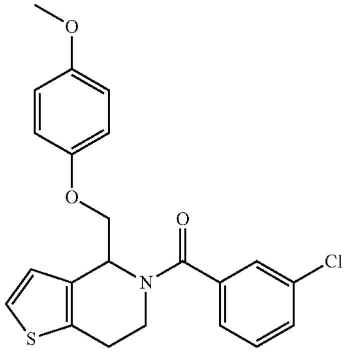
-continued
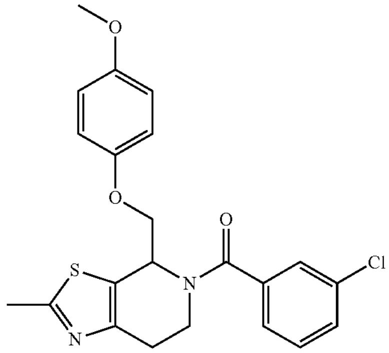
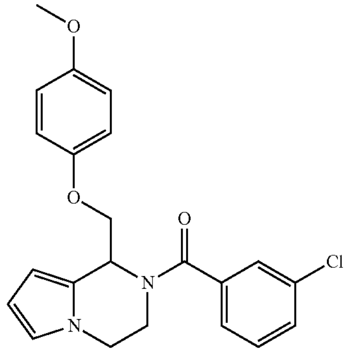
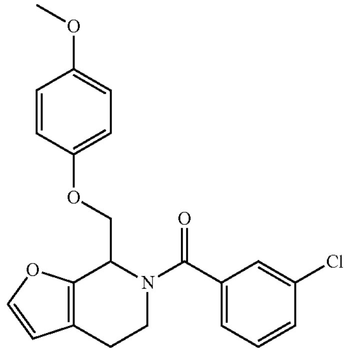
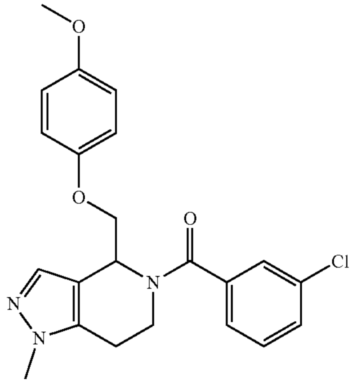

-continued
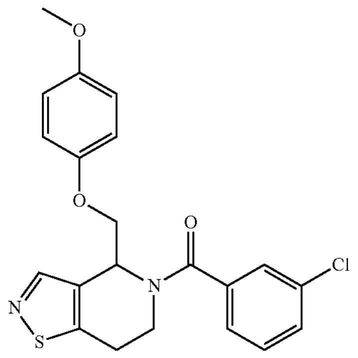
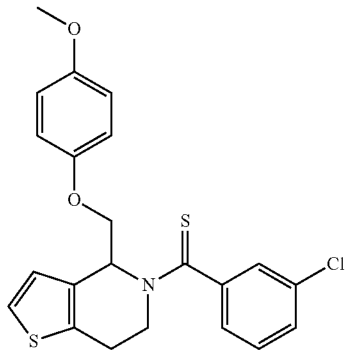
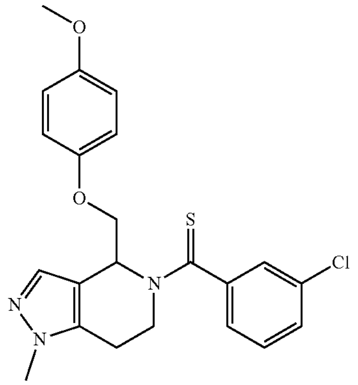
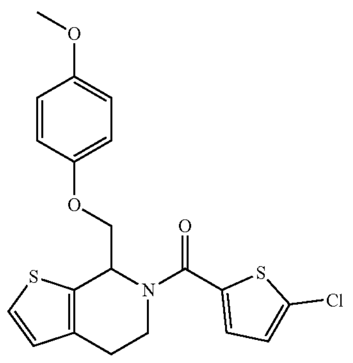
-continued
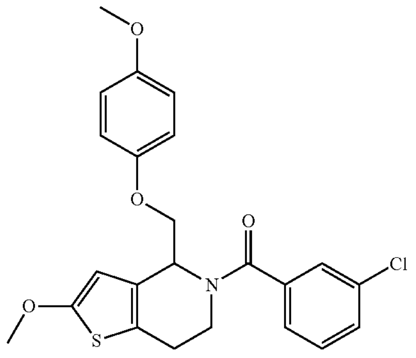
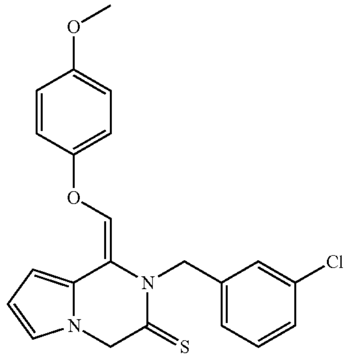
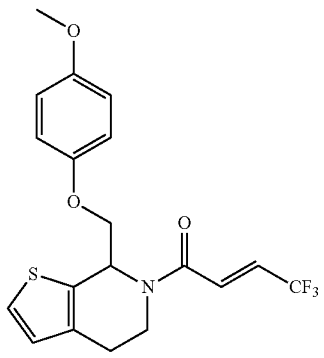
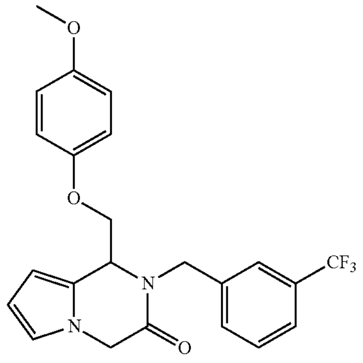

-continued
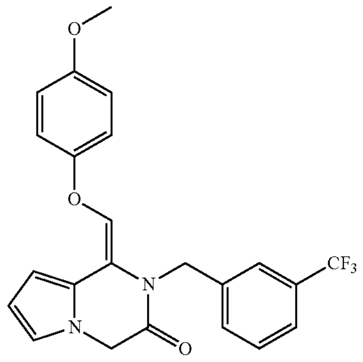
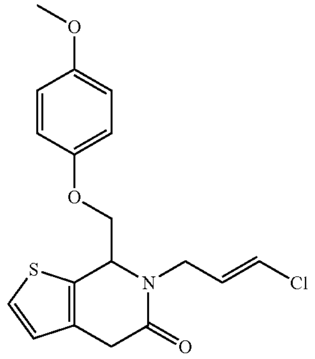
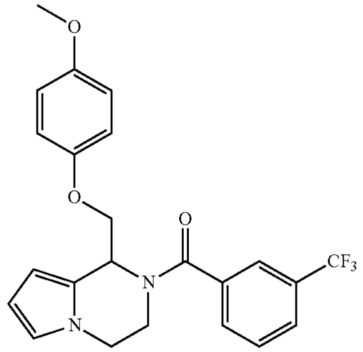
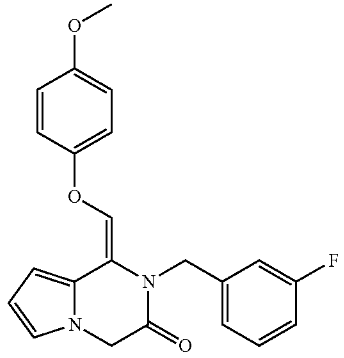
-continued
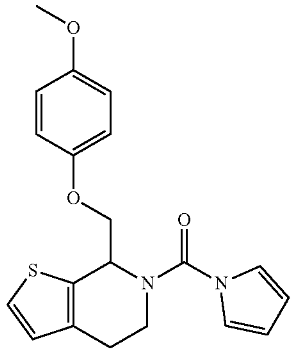
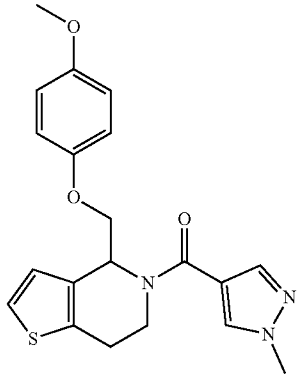
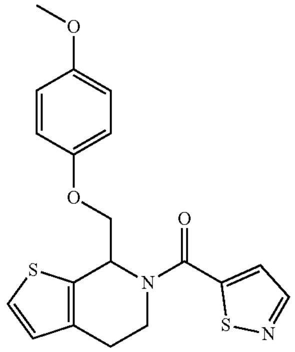
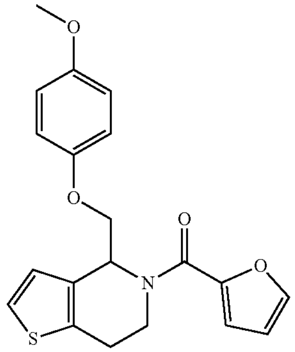

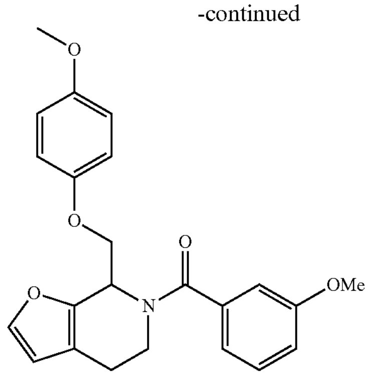
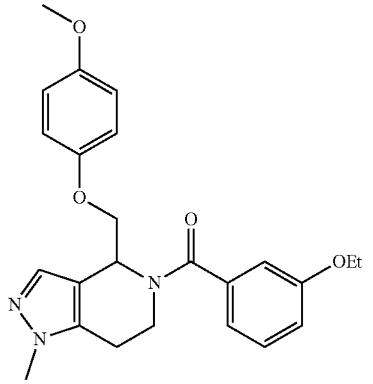
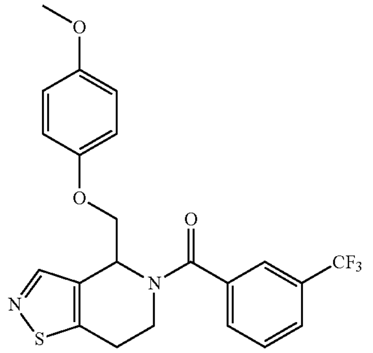
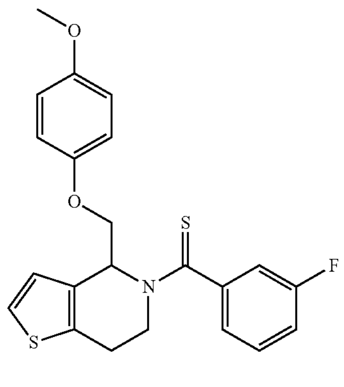
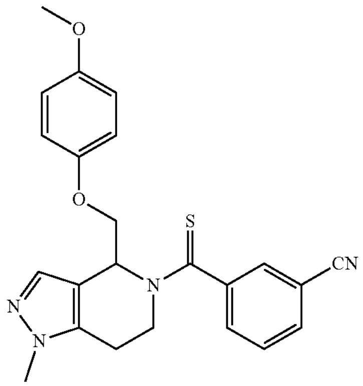
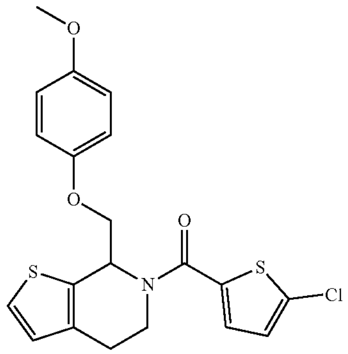
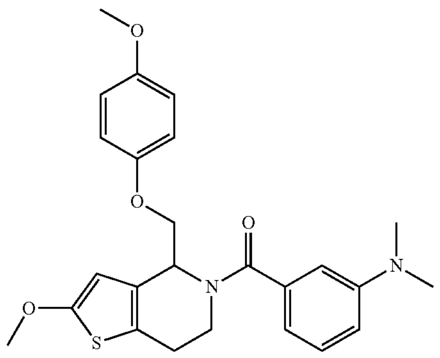
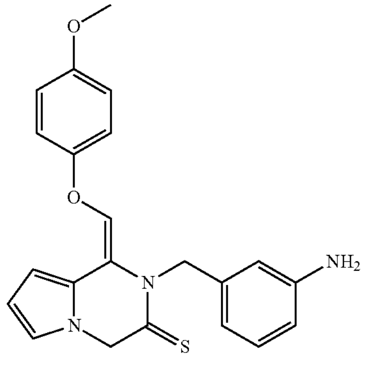

-continued
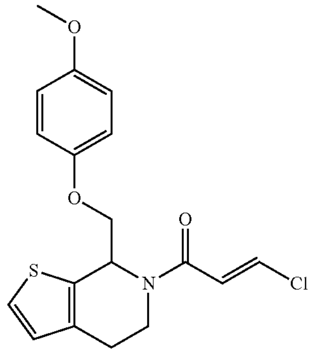
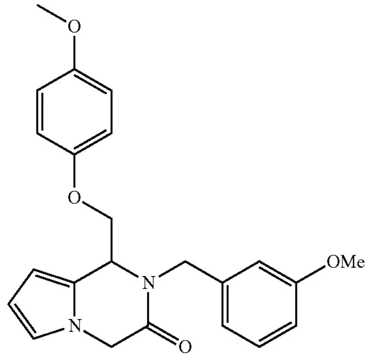
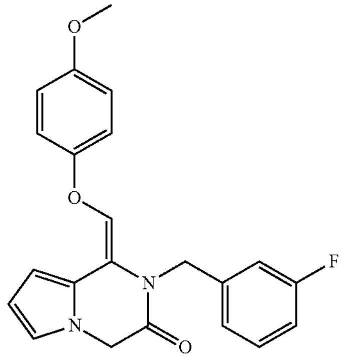
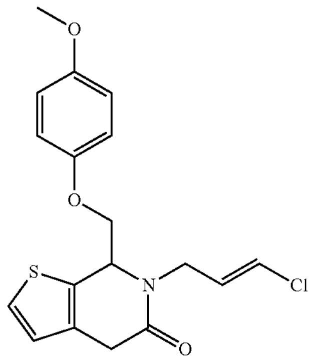
-continued
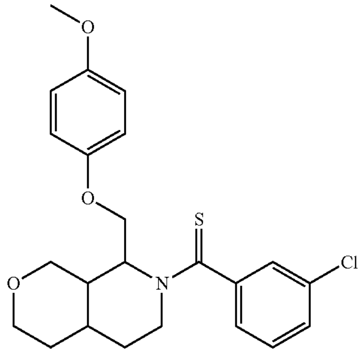
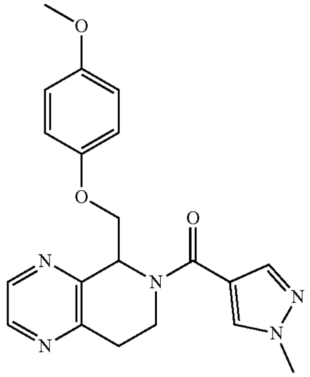
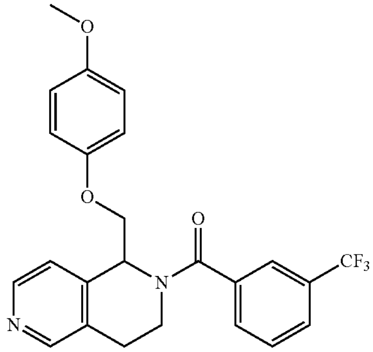
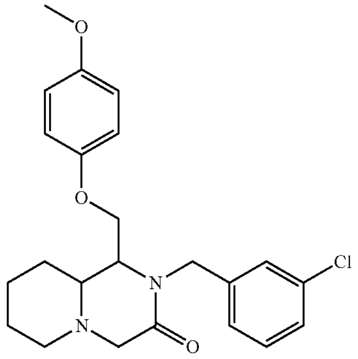

-continued

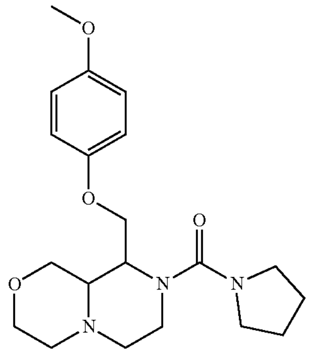

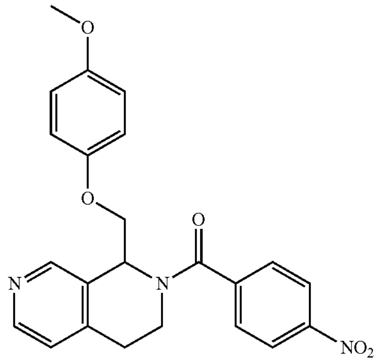

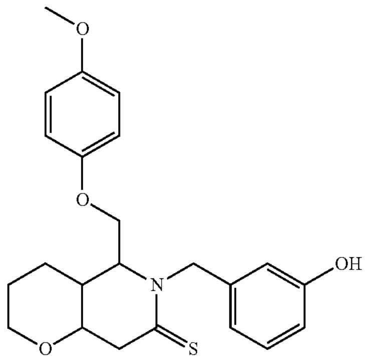

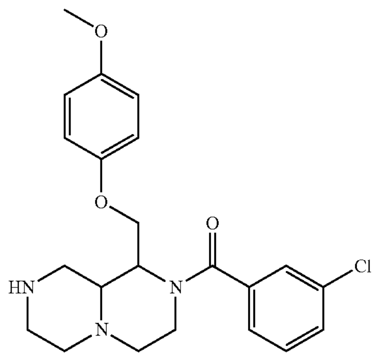

-continued

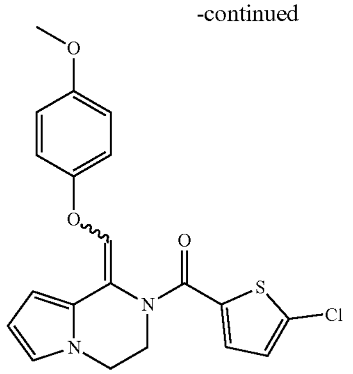

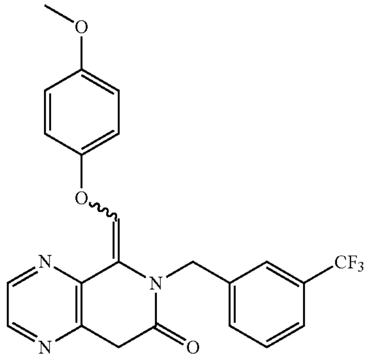

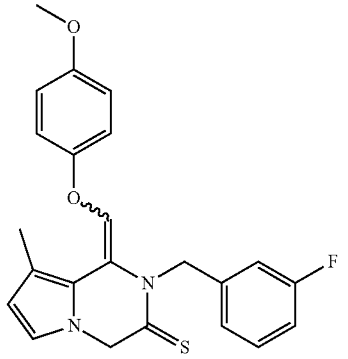

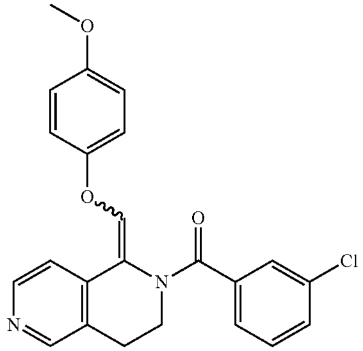

According to a further embodiment there is provided compounds of Formula (I) or salts thereof for use in the treatment of neurological disorders such as Alzheimer's disease Parkinson's disease, schizophrenia, depression, stroke, psychosis and the like.

In another embodiment there is provided a method of treating neurological disorders in a subject in need thereof, the method comprising administering an effective amount of the compound of Formula (I) or salts thereof to the subject.

In certain embodiments, the disclosure contemplates derivatives of compounds disclosed herein such as those containing one or more, the same or different, substituents.

In still another embodiment there is provided a pharmaceutical composition comprising a compound of Formula (I) or salts thereof and a pharmaceutically acceptable excipient. In certain embodiments, the pharmaceutical composition is in the form of a tablet, capsule, pill, gel, granules, aerosol, or aqueous buffer, such as a saline or phosphate buffer, or a nanoparticle formulation, emulsion or liposome, etc. The pharmaceutical composition may also include one or more further active agents, or may be administered in combination with one or more such active agent.

In a yet further embodiment there is provided methods for preparing the compounds of Formula (I) or salts thereof comprising mixing one or more starting materials with reagents under conditions such that the products are formed.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

To the extent that structures provided herein are compounds with tautomers by hydrogen migration, a skilled artisan would understand the formula to cover all tautomeric forms.

As used herein, "alkyl" means a noncyclic straight chain or branched, unsaturated or saturated hydrocarbon such as those containing from 1 to 10 carbon atoms, typically 1 to 4 otherwise designated C1-4alkyl. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge.

An example of an alkylamino is methylamino, (i.e., $—NH—CH_3$).

"Aminoalkyl" refers to an amino group attached through an alkyl bridge as defined above (i.e., $NH_2$-alkyl-).

The terms "halogen" and "halo" refer to fluorine, chlorine, bromine, and iodine.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, $—NRaSO_2Rb$, —C(=O)Ra, —C(=O)ORa, —C(=O)NRaRb, —OC(=O)NRaRb, —ORa, —SRa, —SORa, $—S(=O)_2Ra$, $—OS(=O)_2Ra$ and $—S(=O)_2ORa$. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur or nitrogen atom or replacing an amino group with a hydroxyl group or vice versa. The derivative may be a prodrug. Derivatives may be prepared by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat", "treating" and "treating" are not limited to the case where the subject (e.g. patient) is cured and the disease is eradicated. Rather, embodiments, of the present disclosure also contemplate treatment that merely reduces symptoms, and/or delays disease progression.

Certain of the compounds described herein may contain one or more asymmetric centers and may give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, tautomer forms, hydrated forms, optically substantially pure forms and intermediate mixtures.

As used herein, the term "combination with" when used to describe administration with an additional treatment means that the agent may be administered prior to, together with, or after the additional treatment, or a combination thereof.

Pharmacological tools and potential clinical candidates containing scaffolds for circumventing the current problems experienced by NMDA receptors were designed and executed in the current disclosure and extensive structure activity relationship (SAR) studies were carried out on active hits.

The compounds show a range of subunit selectivity, being most active at GluN2C and GluN2D subunits; some also have differential levels of activity at GluN2A, GluN2A/GluN2B, or all four NMDA receptor subtypes (GluN2A, GluN2B, GluN2C, GluN2D). The GluN2C and GluN2D subunits are expressed in a number of brain locations that make them candidates for treatment of neurological disease. The presence, for example, of GluN2C in the thalamus raises possibility of treating a wide range of affective disorders as well as schizophrenia and Parkinson's disease. The activity at the GluN2D subunit should allow modulation of inhibitory tone in the central nervous system, which could be relevant for cognition, and an unusually wide range of neurological problems. Activities at GluN2B could be relevant for learning, memory, and cognition. This series of modulators all enhance NMDA receptor function, and some show a dependence on the concentration of glutamate. Thus, these are positive allosteric modulators, but in the case where the binding site can accommodate both positive and negative modulators, it is possible for some compounds within this series to also be negative allosteric modulators.

A series of piperidines with various fused heterocycles is described. These piperidines were also hybridized with a dihydroisoquinolinone scaffold where an amide or thioamide bond is moved onto the piperidine ring. Compounds synthesized showed improved potency, efficacy, and drug-like properties compared to the previously disclosed CIQ, while also maintaining selectivity for GluN2C and GluN2D. Other compounds disclosed herein have a low molecular weight and good aqueous solubility.

The above mentioned dihydroisoquinolinone scaffold was discovered based off computational studies done with CIQ and these analogues showed improved efficacy (3-4-fold potentiation) with similar potency (4-12 μM at GluN2C/D) and selectivity (no activity at GluN2A/B) as CIQ.

An extensive SAR was also developed with the dihydroisoquinolinone core maintained throughout, in which the potency was improved to 0.14 μM with 2-fold potentiation at GluN2C/D. Separation of enantiomers via chiral HPLC revealed the activity to be stereodependent, with one enantiomer holding all activity in each case. A crystal structure confirmed the R-(+) enantiomer to be the active stereoisomer.

The piperidine-based scaffold was developed while exploring bioisosteric replacements of the C-ring for both potency and solubility gains. A tetrahydrothienopyridine core showed promising activity (4 μM and 3-fold potentiation at GluN2C/D) while also eliminating multiple metabolically labile anisole groups found on the C-ring of CIQ. Through a series of heterocyclic C-ring replacements focused on improving aqueous solubility, a tetrahydropyrrolopyrazine core was found to maintain similar potency at 2 μM while lowering A Log P nearly a full log unit. Interestingly, hybridizing this tetrahydropyrrolopyrazine core with the dihydroisoquinolinone core to give a dihydropyrrolopyrazinone analogue showed 2-fold potentiation at 0.3 μM and 5-fold maximum potentiation.

This is the first instance in the series of significant activity improvement while maintaining or improving druggable properties. This presents an excellent opportunity for the development of an improved compound and eventually a clinical candidate.

Methods of Use

The compounds described herein can generally be used to treat, prevent or produce a reduction in symptoms of neurologic disorders, which includes abnormalities of the nervous system. These disorders can be characterized by primary location, dysfunction/abnormality or cause. Central nervous system disorders impact the brain or spinal cord, while peripheral nervous system disorders affect the nerves. Causes include, for example, genetic abnormalities, developmental abnormalities, injury, ischemia, or trauma, infection, cancer or diseases and disorders of the vasculature that supplies the nervous system, for example stroke. In certain instances, the neurologic disorder may be associated with NMDA receptor activation.

Disorders that can be treated, prevented or for which symptoms can be reduced include neuropsychiatric disorders, neurodegenerative disorders, as well as neurologic disorders including neuropathic pain, inflammatory pain, stroke, traumatic brain injury, epilepsy, transient ischemica, global ischemia, hypoxia, spinal cord trauma and other neurologic events.

In certain embodiments, the compounds are used for the treatment or prevention of neuropsychiatric disorders. These disorders include, without limitation, depression, anxiety, bipolar disorder, obsessive-compulsive disorder, alcohol and substance abuse, and attention-deficit hyperactivity disorder.

In certain other embodiments, the compounds are used for the treatment or prevention of neurodegenerative disorders. These disorders are typically characterized by gradual and progressive nervous system dysfunction due to loss of neuronal cells and neuronal tissue and include, without limitation, Alzheimer's disease, Parkinson's disease, Huntington's disease, Amyotrophic lateral sclerosis (ALS/Lou Gehrig's disease), Multiple Sclerosis, spinal muscular atrophy, spinal and bulbar muscular atrophy, familial spastic paraparesis, Machado Joseph disease Friedreich's ataxia and Lewy body disease.

In certain embodiments, a method of treatment of a neurologic disorder is provided including administering a compound of Formula I, or a pharmaceutically acceptable salt, ester or prodrug thereof, to a host in need thereof. In certain embodiments, the disorder is associated with NMDA receptor activation. In one embodiment, the disorder is a neuropsychiatric disorder. In another embodiment, the disorder is a neurodegenerative disorder. In certain other embodiments, the disorder is neuropathic pain. In yet further embodiments, the disorder is an injury resulting from an ischemic event or neuropathic injury or infection.

In certain embodiments, methods are provided to prevent neurodegeneration in patients with Parkinson's, Alzheimer's, Huntington's chorea, ALS, and other neurodegenerative conditions.

Uses of the compounds in the treatment or manufacture of a medicament for such disorders are also provided.

In certain embodiments, a method of treatment or prevention of neurologic disorder, such as a neuropsychiatric or neurodegenerative disease or disorder or a disorder resulting from injury, trauma, infection or ischemia, in a host is provided including administering a compound of Formula I or a pharmaceutically acceptable salt, ester or prodrug thereof to the host, either alone or in combination, in which the host is suffering from a reduced pH in a region of the brain. In certain embodiments, a disorder has caused a region with a pH below pH 7.6, or below 7.5, or below 7.4, or below 7.3, or below 7.2, or below 7.1, or below 7, or below 6.9, or below 6.8, or below 6.7, or below 6.6 or below 6.5 or below 6.4. In certain embodiments, the reduced pH is due to pathological conditions such as hypoxia resulting from stroke, traumatic brain injury, global ischemia, such as global ischemia that may occur during cardiac surgery, hypoxia, including hypoxia that may occur following cessation of breathing, pre-eclampsia, spinal cord trauma, epilepsy, status epilepticus, neuropathic pain, inflammatory pain, chronic pain, vascular dementia and glioma tumors.

In one embodiment, methods are provided to attenuate the progression of an ischemic or excitotoxic cascade by administering a compound of Formula I. In addition, methods are provided to decrease infarct volume by administering a compound of Formula I. Still further, methods are provided to decrease behavioral deficits associated with an ischemic event by administering a compound of Formula I. In one embodiment, methods are provided to treat patients with ischemic injury or hypoxia, or prevent or treat the neuronal toxicity associated with ischemic injury or hypoxia, by administering a compound or composition described herein. In one particular embodiment, the ischemic injury is stroke. In another particular embodiment, the ischemic injury is vasospasm after subarachnoid hemorrhage. In other embodiments, the ischemic injury is selected from, but not limited to, one of the following: traumatic brain injury, cognitive deficit after bypass surgery, cognitive deficit after carotid angioplasty; and/or neonatal ischemia following hypothermic circulatory arrest.

Further, compounds selected according to the methods or processes described herein can be used prophylactically to prevent or protect against such neurologic or neuropathologic diseases, disorders or conditions, such as those described herein. In one embodiment, patients with a predisposition for an ischemic event, such as a genetic predisposition, can be treated prophylactically with the methods and compounds described herein. In another embodiment, patients at risk for or exhibiting vasospasms can be treated prophylactically with the methods and compounds described herein. In a further embodiment, patients undergoing cardiac bypass surgery can be treated prophylactically with the methods and compounds described herein. In one embodiment, the compounds of the present disclosure can be used as neuroprotectants.

In another embodiment, methods are provided to treat patients with neuropathic pain or related disorders by administering a compound or composition described herein. In certain embodiments, the neuropathic pain or related disorder can be selected from the group including, but not limited to: peripheral diabetic neuropathy, postherpetic neuralgia, complex regional pain syndromes, peripheral neuropathies, chemotherapy-induced neuropathic pain, cancer neuropathic pain, neuropathic low back pain, HIV neuropathic pain, trigeminal neuralgia, and/or central post-stroke pain. This dysfunction can be associated with common symptoms such as allodynia, hyperalgesia, intermittent abnormal sensations, and spontaneous, burning, shooting, stabbing, paroxysmal or electrical-sensations, paresthesias, hyperpathia and/or dysesthesias, which can also be treated by the compounds and methods described herein.

Further, the compounds and methods described herein can be used to treat neuropathic pain resulting from peripheral or central nervous system pathologic events, including, but not limited to trauma; ischemia; infections or endocrinologic disorders, including, but not limited to, diabetes mellitus, diabetic neurophathy, amyloidosis, amyloid polyneuropathy (primary and familial), neuropathies with monoclonal proteins, vasculitic neuropathy, HIV infection, herpes zoster-shingles and/or postherpetic neuralgia; neuropathy associated with Guillain-Barre syndrome; neuropathy associated with Fabry's disease; entrapment due to anatomic abnormalities; trigeminal and other CNS neuralgias; malignancies; inflammatory conditions or autoimmune disorders, including, but not limited to, demyelinating inflammatory disorders, rheumatoid arthritis, systemic lupus erythematosus, Sjogren's syndrome; and cryptogenic causes, including, but not limited to idiopathic distal small-fiber neuropathy. Other causes of neuropathic pain that can be treated according to the methods and compositions described herein include, but are not limited to, exposure to toxins or drugs (such as arsenic, thallium, alcohol, vincristine, cisplatinum and dideoxynucleosides), dietary or absorption abnormalities, immuno-globulinemias, hereditary abnormalities and amputations (including mastectomy). Neuropathic pain can also result from compression of nerve fibers, such as radiculopathies and carpal tunnel syndrome.

In a further embodiment, methods are provided to treat patients with neurodegenerative diseases by administering a compound selected according to the methods or processes described herein. These neurodegenerative disorders include, without limitation, Alzheimer's disease, Parkinson's disease, Huntington's disease, Amyotrophic Lateral Sclerosis (ALS/Lou Gehrig's disease), Multiple Sclerosis, spinal muscular atrophy, spinal and bulbar muscular atrophy, familial spastic paraparesis, Machado Joseph disease, Friedreich's ataxia and Lewy body disease. In one embodiment, the neurodegenerative disease can be Parkinson's disease. In another embodiment, the neurodegenerative disease can be Alzheimer's disease. In another embodiment, the neurodegenerative disease can be Huntington's disease and/or ALS.

In another embodiment, methods are provided to treat patients with brain tumors by administering a compound selected according to the methods or processes described herein. In some embodiments, the compounds are useful in the treatment of tumor growth. In certain embodiments, the compounds reduce tumor mass. In one embodiment, the compounds are useful in the treatment or prophylaxis of a neurologic event involving acidification of brain or spinal cord tissue. In another embodiment, the NMDA receptor antagonists of this disclosure are useful both in the treatment of stroke and head trauma, and for use as prophylactic agents for at risk patients. The acid generated by ischemic tissue during stroke is harnessed since the neuroprotective agents described herein are more potent at acidic pH. In this way side effects are minimized in unaffected tissue since drug at these sites are less potent. These compounds may be used to reduce the amount of neuronal death associated with stroke and head trauma. They may be given chronically to individuals with epilepsy or who are at risk for stroke or head trauma, preoperatively in high risk heart/brain surgery, etc., in order to lengthen the window of opportunity for subsequent therapy.

In addition, methods are provided to treat the following diseases or neurological conditions, including, but not limited to: chronic nerve injury, chronic pain syndromes, such as, but not limited to diabetic neuropathy, ischemia, ischemia following transient or permanent vessel occlusion, seizures, spreading depression, restless leg syndrome, hypocapnia, hypercapnia, diabetic ketoacidosis, fetal asphyxia, spinal cord injury, traumatic brain injury, status epilepticus, epilepsy, hypoxia, perinatal hypoxia, concussion, migraine, hypocapnia, hyperventilation, lactic acidosis, fetal asphyxia during parturition, brain gliomas, and/or retinopathies by administering a compound selected according to the methods or processes described herein.

In certain embodiments, the compounds are used for the treatment or prevention of neuropsychiatric disorders. Generally, these disorders are mental disturbances attributable to diseases of the nervous system. These disorders include depression, anxiety, bipolar disorder, obsessive-compulsive disorder, alcohol and substance abuse, and attention-deficit hyperactivity disorder. In particular embodiments, the disorders are neuropsychiatric mood disorders, non-limiting examples of which include depression, including major depression, treatment-resistant depression and treatment-resistant bipolar depression, bipolar disorders including cyclothymia (a mild form of bipolar disorder), affective disorders such as SAD (seasonal affective disorder) and mania (euphoric, hyperactive, over inflated ego, unrealistic optimism). In certain embodiments, the disorder is treatment-resistant depression or treatment-resistant bipolar depression. Neuropsychiatric disorders also include attention deficit disorders such as ADD or ADHD. In certain embodiments, a method of treatment a neuropsychiatric disorder is provided including administering a compound of the disclosure, alone or in combination to a host diagnosed with the disorder. Uses of the compounds in the treatment or manufacture of a medicament for such disorders are also provided.

In certain embodiments, the compounds are used for the treatment of depression in a host diagnosed with the disorder. In certain other embodiments, the compounds are used for treatment of a bipolar disorder in a host diagnosed with the disorder. The compounds can also be used to diminish the severity of depressive or manic episodes or prevent future episodes. In certain embodiments, methods of treating seasonal disorders is provided including administering the compound to a host at risk of suffering from a SAD. In particular, the compounds can be provided on a seasonal basis. In some embodiments, the host has been diagnosed as suffering from or is at risk for SAD or depression. In certain embodiments, the host is at risk of suffering from a mania. The mania can be characterized by euphoria, hyperactivity, over-inflated ego, or unrealistic optimism. In certain embodiments, the host is suffering from an attention deficit disorders, for example ADD or ADHD.

Depression, formally called major depression, major depressive disorder or clinical depression, is a medical illness that involves the mind and body. Most health professionals today consider depression a chronic illness that requires long-term treatment, much like diabetes or high blood pressure. Although some people experience only one episode of depression, most have repeated episodes of depression symptoms throughout their life. Depression is also a common feature of mental illness, whatever its nature and origin. In other instances, the host does not have a history of a major psychiatric disorder but has been diagnosed with suffering from at least one depressive episode. In other instances, the host has been diagnosed with bipolar disorder. The host may also have been diagnosed as suffering from panic attacks or anxiety.

In some instances, the host is not suffering from a chronic disorder but is at risk of a depressive episode, anxiety or a panic attack due to environmental circumstances. The compounds may be given prophylactically to prevent onset of such an episode. For instance, in certain instances the compounds can be provided to a host before a plane trip, a public speech, or other potential stressful even that could lead to an episode. In some embodiments, therefore, a method of prevention of a neuropsychiatric episode is provided, including administering a compound of the disclosure to a host at risk of suffering from such an episode. In some instances, the compounds are useful for treatment or prophylaxis of disorders such as depression or bipolar disorder associated with an injury or with aging.

In certain embodiments, the compounds are administered to a host suffering from or at risk of suffering from age-related depression. The compounds can be administered prophylactically to a host over the age of 60, or over the age of 70, or over the age of 80 to prevent or reduce the severity of depressive episodes.

In certain embodiments, compounds of the present disclosure can be used to activate or stimulate the mTOR signaling pathway. In one embodiment, the compounds can be used to modulate mTOR activity in the brain, for example in the prefrontal cortex. Compounds which modulate or stimulate mTOR signaling may be useful in the treatment or prophylaxis of depression and other neuropsychiatric disorders.

In a particular embodiment, compounds of the present disclosure may be used to treat traumatic brain injury caused by a blast or a blast injury.

In one embodiment, the compounds may be used to in the treatment of schizophrenia. In another embodiment, the compounds may not be used to treat schizophrenia.

NMDARs play an important role in processes such as synaptic plasticity, learning, and memory. Deficits in synaptic plasticity are thought to contribute to cognitive dysfunction in a wide range of indications, including Alzheimer's disease, autism, developmental delay, cognitive disability, schizophrenia, Parkinson's disease and other neurological diseases.

In certain embodiments, the disclosure relates to methods of treating or preventing a neurological disease, condition, or disorder comprising administering an effective amount of a tetrahydroisoquinoline compound or derivative disclosed herein to a subject in need thereof. In certain embodiments, the condition is depression, anxiety, schizophrenia, or bipolar disorder. In certain embodiments, the compound may be administered in combination with a second psychiatric medication, e.g., anti-depressant, anti-psychotic (typical or atypical), relaxant, chlorpromazine, haloperidol, perphenazine, fluphenazine, risperidone, olanzapine, quetiapine, ziprasidone, aripiprazole, paliperidone, etc.

In certain embodiments, the condition is a central nervous system (CNS) disorders such as those selected from Alzheimer's disease, Huntington's disease, and Amyotrophic Lateral Sclerosis (ALS). In certain embodiments, the disclosure relates to methods of improving learning or memory comprising administering an effective amount of a compound disclosed herein to a subject in need thereof.

In certain embodiments, the disclosure relates to methods of improving synaptic plasticity, learning, and memory by administering compounds disclosed herein to subject in need thereof. Deficits in synaptic plasticity are thought to contribute to cognitive dysfunction in a wide range of indications, including Alzheimer's disease, autism, developmental delay, cognitive disability, schizophrenia, Parkinson's disease and other neurological diseases. In certain embodiments, the disclosure relates to methods of treating or preventing Alzheimer's disease, autism or autism spectrum disorders, developmental delay, cognitive disability, schizophrenia, Parkinson's disease and other neurological diseases comprising administering compounds disclosed herein to a subject in need thereof.

Certain NMDARs contain a GluN1 subunit in addition to GluN2A-GluN2D subunits. Stimulation of one or more of the subunits are thought to be beneficial for the treatment of these conditions as well as other conditions dependent on synaptic plasticity such as motor retraining and rehabilitation after ischemic insult, traumatic brain injury, spinal cord injury, and conditions that involve impairment of movement, speech, vision, or other normal functions controlled by the brain. In certain embodiments, the disclosure relates to methods of managing, improving, treating or preventing motor retraining and rehabilitation after ischemic insult, traumatic brain injury, and conditions that involve in impairment of movement, speech, vision, or other functions controlled by the brain by administering an effective amount of a compound disclosed herein to a subject in need thereof.

In some embodiments, the disease or condition is depression, anxiety, epilepsy, posttraumatic stress disorder, dementia, diabetic neuropathy, peripheral neuropathy, or stroke.

In certain embodiments, the methods described herein include a method of treating or reducing the risk of disorders associated with neurological disorders, and neuropsychiatric disorders in a subject. Examples of neurological and neuropsychiatric disorders include depression, anxiety, Alzheimer's, CNS injuries, and the like. This method includes the steps of selecting a subject with or at risk of developing the neurological disorder or neuropsychiatric disorder and administering to the subject a therapeutically effective amount of a compound disclosed herein. The compound can be administered systemically (e.g., orally), parenterally (e.g., intravenously), intramuscularly, intreperitoneally, transdermally (e.g., by a patch), extracorporeally, topically, by inhalation, subcutaneously or the like), by administration into the central nervous system (e.g., into the brain (intracerebrally or intra ventricularly), spinal cord, or into the cerebrospinal fluid), or any combination thereof.

The subject in need thereof can be a patient diagnosed as suffering from depression or anxiety. These diseases and their diagnoses are very clearly defined in the "Diagnostic and Statistical Manual of Mental Disorders (DSM-IV)" published by the American Psychiatric Association. This manual sets forth diagnostic criteria, descriptions and other information to guide the classification and diagnosis of mental disorders and is commonly used in the field of neuropsychiatry. In certain embodiments, the subject receiving a pharmaceutical composition containing a compound disclosed herein may be co-administered an antidepressant or anti-anxiolytic medication (in combination with as a single dose or separate medication). In certain embodiments, the patient has been diagnosed by a mental health professional (e.g., a psychiatrist) with an anxiety or depression disorder.

In certain embodiments, the disclosure contemplates the treatment of other mental disorders or conditions by administering effective amounts of compounds disclosed herein. contemplated mental disorders and conditions include, but are not limited to, acute stress disorder, adjustment disorder, adolescent antisocial behavior, adult antisocial behavior, age-related cognitive decline, agoraphobia, alcohol-related disorder, Alzheimer's, amnestic disorder, anorexia nervosa, anxiety, attention deficit disorder, attention deficit hyperactivity disorder, autophagia, bereavement, bibliomania, binge eating disorder, bipolar disorder, body dysmorphic disorder, bulimia nervosa, circadian rhythm sleep disorder, cocaine-addition, dysthymia, exhibitionism, gender identity disorder, Huntington's disease, hypochondria, multiple personality disorder, obsessive-compulsive disorder (OCD), obsessive-compulsive personality disorder (OCPD), posttraumatic stress disorder (PTSD), Rett syndrome, sadomasochism, and stuttering.

In certain embodiments, the disclosure contemplated the treatment of depression with compounds disclosed herein. Depression can be divided into several types. Major depression is the most severe form of depression characterized by a severe, persistent depressed mood and loss of interest or pleasure in normal activities accompanied by decreased energy, changes in sleep habits, restless behavior, difficulty concentrating, loss of appetite, feelings of guilt or hopelessness, and in severe cases, psychotic symptoms such as hallucinations, delusions, and even suicidal thoughts. An individual typically has a history (greater than 2 weeks) of persistent sad moods, loss of interest or pleasure in activities once enjoyed, and feelings of guilt or hopelessness, restless behavior, difficulty concentrating, and even suicidal thoughts in order to make a diagnosis of major depression. The Beck's Depression Scale Inventory, or other screen tests for depression, can be helpful in diagnosing depression.

Major depression can be treated with medications and/or counseling. Medications used include, but are not limited to, tricyclic antidepressants, monoamine oxidase inhibitors, selective serotonin re-uptake inhibitor (SSRIs), and some antidepressant drugs such as bupropion, reboxetine, trazodone, venlafaxine, and mitrazapine. Antipsychotic medications are typically administered to patients suffering from more severe forms of psychotic symptoms, such as delusions or hallucinations. Types of psychotherapy include interpersonal therapy, group therapy, and cognitive behavioral therapy.

Alternative therapeutic methods include the use of herbal products for management of chronic conditions, such as psychiatric disorders, including anxiety and depression.

A second form of depression is chronic low-grade depression, also known as dysthymia. Dysthymia is present most of the time for a period of two or more years wherein an individual experiences a decrease in his/her overall level of energy, appetite, and sleep, as well as has feelings of low self-esteem and hopelessness. These symptoms cause distress and the individual has difficulty functioning in everyday activities. These symptoms, however, are not as severe as those symptoms experienced in major depression. The cause and maintenance of these symptoms are typically due to one of the following problems: loss of a friend, substantial disappointment at work or home, prolonged or chronic illness, and alcohol or drug abuse. People who suffer from dysthymia are at an increased risk for episodes of major depression. This produces a behavioral pattern called "double depression" wherein the individual is mildly depressed most of the time, with periodic symptoms of major depression.

The least severe form of depression is a depressed mood. This is an emotional state dominated by feelings of sadness, gloominess, or emptiness, which may be associated with lack of energy. Depressed moods are usually temporary responses to an unhappy or stressful event.

In certain embodiments, the disclosure contemplated the treatment of autism spectrum disorders with compounds disclosed herein. Autism Spectrum Disorder, including Asperger Syndrome, is a spectrum of neurodevelopmental disorders characterized by dysfunction in three core behavioral dimensions: repetitive behaviors, social deficits, and cognitive deficits. The repetitive behavior domain involves compulsive behaviors, unusual attachments to objects, rigid adherence to routines or rituals, and repetitive motor mannerisms such as stereotypies and self-stimulatory behaviors. The social deficit dimension involves deficits in reciprocal social interactions, lack of eye contact, diminished ability to carry on conversation, and impaired daily interaction skills. The cognitive deficits can include language abnormalities.

Administration of compounds disclosed herein may be when a child or infant shows the early signs of signs of autism spectrum disorder or other abnormal social or behavioral development, or about the time of developmental landmarks in infants or children that show early signs of autism spectrum disorder or other abnormal or behavioral development. A therapeutic intervention administered during this period could reset the developmental trajectory of the child preventing the acquisition of second order social impairments.

In certain embodiments, the disclosure contemplated the treatment of bipolar disorders with compounds disclosed herein. Bipolar disorder affects men and women equally and typically appears between the ages of 15 and 25. As opposed to unipolar major depression, the incidence of bipolar disorder does not vary widely around the world. The exact cause is unknown, but it is linked to areas of the brain which regulate mood, and has a strong genetic component. The American Psychiatric Association's "Diagnostic and Statistical Manual of Mental Disorders" describes two types of bipolar disorder, type I and type II. The type I (formerly known as manic depressive disorder), there has been at least one full manic episode. People with this type, however, may also experience episodes of major depression. In type II disorder, periods of "hypomania" involve more attenuate (less severe) manic symptoms that alternate with at least one major depressive episode. When the patients have an acute exacerbation, they may be in a manic state, depressed state, or mixed state. The manic phase is characterized by elevated mood, hyperactivity, over-involvement in activities, inflated self-esteem, a tendency to be easily distracted, or little need for sleep. In the depressive phase, there is loss of self-esteem, withdrawal, sadness, or a risk of suicide. Either the manic or the depressive episodes can predominate and produce a few mood swings, or the patterns of the mood swing may be cyclic. While in either phase, patients may abuse alcohol or other substances, which worsens the symptoms.

Methods for treating bipolar disorders differ depending upon the state of the patient. During an acute phase, hospitalization may be required to control the symptoms. In order to reduce the risk of switching into mania, hypomania or rapid cycling, a combination of a mood stabilizer (e.g. lithium; valproate) and/or antidepressants (e.g., bupropion) is utilized for controlling bipolar disorders. Even though lithium is often utilized in controlling manic and depressive relapses, careful medical supervision along with maintaining salt intake, avoiding non-steroidal anti-inflammatory drugs, and undertaking weight-reduction diets are typically performed in order to reduce possible renal failure. Valproate also is characterized by severe side effects including nausea, vomiting, anorexia, heartburn, and diarrhea. Finally, the use of antidepressants for suppressing bipolar disorder is typically monitored in order to achieve symptomatic remission. Therefore, safer therapeutic methods are needed in the art in order to reduce the severe side effects associated with current treatments of bipolar disorders.

In certain embodiments, the disclosure contemplated the treatment of cyclothymic disorders with compounds disclosed herein. Cyclothymic disorders are similar to bipolar disorders, but less extreme. Cyclothymic disorders are characterized by stages of mild mood changes with stages of mild depression and excitement (hypomania). The changes in mood are very irregular and abrupt, but the severity of the swings is less. Cyclothymia is treated like bipolar disorders, though often not as aggressively. Thus, safer treatments are needed in the art.

In certain embodiments, the disclosure contemplated the treatment of anxiety disorders with compounds disclosed herein. Anxiety disorders, panic attacks, and agoraphobia are conditions that occur as a manifestation of primary mood disorders such as depression. Anxiety is a feeling of apprehension or fear that lingers due to an individual's perception of persistent and unrelenting stress. Anxiety is typically accompanied by various physical symptoms including twitching, trembling, muscle tension, headaches, sweating (e.g., night sweats), dry mouth, or difficulty swallowing. Some people also report dizziness, a rapid or irregular heart rate, increased rate of respiration, diarrhea, or frequent need to urinate when they are anxious. Fatigue, irritable mood, sleeping difficulties, decreased concentration, sexual problems, or nightmares are also common. Some people are more sensitive to stress and are thus more likely to develop anxiety disorders. The propensity to succumb to anxiety attacks may be due to genetic predisposition or by previous (e.g. childhood) exposure to certain stresses.

Treatment of anxiety disorders includes diagnostic tests for blood differential and thyroid function as well as an electrocardiogram (EKG). If any worrisome physical signs or symptoms do not accompany the anxiety, a referral to a mental health care professional is recommended. Psychotherapy such as cognitive-behavior therapy (CBT) along with the medication benzodiazepines is typical in severe cases of anxiety. The use of addition to these treatments, use of antidepressants such as imipramine and the selective serotonin re-uptake inhibitor (SSRI) paroxetine are also contemplated.

In certain embodiments, the disclosure contemplated the treatment of panic disorders with compounds disclosed herein. Panic disorder, one of the anxiety disorders, is characterized by repeated and unexpected attacks of intense fear and anxiety. Panic attacks are usually not related to a particular situation and typically "peak" within ten minutes of their onset. The exact cause of panic disorder is unknown, but it is associated with multiple physiological factors. Panic disorder can occur with or without agoraphobia, but agoraphobia develops in one-third of cases.

In certain embodiments, the disclosure contemplated the treatment of agoraphobia with compounds disclosed herein. Agoraphobia is a disorder characterized by avoidance of crowds, and open and public places, particularly if escape or assistance is not immediately available. The development of agoraphobia may involve learned behavior, since it reflects a fear of experiencing panic attacks in unprotected settings, and sometimes the association of panic attacks with areas where they have occurred.

Symptoms of panic disorder include shortness of breath, dizziness, palpitations, trembling, sweating, choking, nausea, numbness, chest pain, hot flashes or chills, fear of dying, fear of losing control, or fear of going insane. Symptoms of agoraphobia include anxiety about being in places where escape might be difficult, fear of being alone, fear of losing control in a public place, feeling of helplessness, or feelings of detachment.

In certain embodiments, the disclosure contemplated the treatment of attention deficit disorders (ADD) with compounds disclosed herein. Symptoms include developmentally inappropriate levels of attention, concentration, activity, distractibility, and impulsivity. There are three subcategories of attention deficit disorder: (1) attention deficit/hyperactivity disorder of the combined type; (2) attention deficit/hyperactivity disorder of the predominantly inattentive type; and (3) attention deficit/hyperactivity disorder of the predominantly hyperactive or impulsive type.

In certain embodiments, the disclosure contemplated the treatment of sleep disorders with compounds disclosed herein. A sleep disorder is a disruptive pattern of sleep that may include difficulty: falling or staying asleep, falling asleep at inappropriate times, excessive total sleep time, or abnormal behaviors associated with sleep. There are more than 100 different disorders of sleeping and waking. They can be grouped into four main categories: problems with staying and falling asleep (e.g., insomnia), problems with staying awake (e.g., sleep state misperception), problems with adhering to a regular sleep schedule (e.g., hypersomnias such as narcolepsy), and sleep disruptive behaviors (e.g., sleep walking). Both insomnia and sleep disruptive behaviors could be direct results of a patient suffering from a psychological disorder such as depression or anxiety.

In certain embodiments, the disclosure contemplated the treatment of insomnia with compounds disclosed herein. Insomnia includes any combination of difficulty with falling asleep, staying asleep, intermittent wakefulness, and early-morning awakening and can lead to the following disorders: psychophysiological, delayed sleep phase syndrome, hypnotic dependent disorder, and stimulant dependent sleep disorder. Episodes may be either transient (2-3 weeks) or chronic.

Sleep disruptive behaviors include sleep terror disorder, sleep walking or REM behavior disorders (a type of psychosis related to lack of REM sleep and lack of dreaming). Symptoms of sleep disruptive behaviors are depressed mood, anxiety, apathy, difficulty concentrating, irritability, daytime fatigue, drowsiness, and difficulty falling asleep.

In one aspect of the present disclosure, the psychiatric disorder to be treated is PTSD. PTSD is defined by DSM-IV as an anxiety disorder that an individual may develop following exposure to a traumatic event, and is characterized by (1) re-experiencing the traumatic event, such as recurrent nightmares, intrusive recollections of the event, flashbacks, physiological and psychological responses to internal or external cues relating to the event, etc.; (2) persistent avoidance of thoughts, people or places associated with the event; (3) numbing of general responsiveness such as emotional detachment, restricted affect or loss of interest in activities; and (4) persistence of increased arousal such as exaggerated startle response, hypervigilance, irritability, or difficulty sleeping, etc.

In certain embodiments, the disclosure contemplates the treatment of schizophrenia with compounds disclosed herein. Schizophrenia is characterized by a breakdown of thought processes and by poor emotional responsiveness and is generally accompanied by social or occupational dysfunction. It is often described in terms of positive and negative symptoms. Positive symptoms can include delusions, disorganized speech and thinking, and tactile, auditory, visual, olfactory, and gustatory hallucinations, typically regarded as manifestations of psychosis. Negative symptoms are deficits of normal emotional responses or of other thought processes such as flat or blunted affect and emotion, poverty of speech, inability to experience pleasure, lack of desire to form relationships, and lack of motivation.

The onset of schizophrenia symptoms typically occurs in young adulthood. Diagnosis typically involves the patient meeting three criteria. The first is characteristic symptoms, in which the patient experiences two or more symptoms for more than one month including delusions, hallucinations, disorganized speech, catatonic behavior, and negative symptoms. The second is social or occupational dysfunction. The third is a significant duration, generally about six months.

A subject undergoing treatment with the methods of the disclosure may exhibits an improvement in one or more symptoms associated with the psychiatric disorder. For a description of the relevant symptoms, see, for example, the DSM-IV ((1994) Diagnostic and Statistical Manual of Mental Disorders (4th ed., American Psychiatric Association, Washington D.C.)), which is herein incorporated by reference. The efficacy of the methods of the disclosure can be assessed using any clinically recognized assessment method for measuring a reduction of one or more symptoms of the particular psychiatric disorder. "Alleviation of symptoms," in the context of a behavioral disorder, refers to improvement in the social or psychological function or health of a patient, as evaluated by any measure accepted in the art. Preferably, "alleviation of symptoms" is a clinically recognizable decrease in symptoms described in DSM-IV-TR (American Psychiatric Association, 2000). The psychosocial function of a patient may be evaluated using standard measures provided in DSM-IV-TR (American Psychiatric Association, 2001), such as the Global Assessment of Functioning Scale and the Social and Occupational Functioning Assessment Scale.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound of the disclosure contains a hydrogen-donating heteroatom (e.g., NH), the disclosure also covers salts and/or isomers formed by the transfer of the hydrogen atom to a basic group or atom within the molecule.

Pharmaceutically acceptable salts of the compounds include the acid addition and base salts thereof. Suitable acid addition salts are formed from acids, which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases, which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier, which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrug can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. It is well within the ordinary skill of the art to make an ester prodrug, e.g., acetyl ester of a free hydroxyl group. It is well known that ester prodrugs are readily degraded in the body to release the corresponding alcohol. See e.g., Imai, Drug Metab Pharmacokinet. (2006) 21(3): 173-85, entitled "Human carboxylesterase isozymes: catalytic properties and rational drug design."

Pharmaceutical compositions for use in the present disclosure typically comprise an effective amount of a compound and a suitable pharmaceutical acceptable carrier. The preparations may be prepared in a manner known per se, which usually involves mixing at least one compound according to the disclosure with one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of at least one compound of the disclosure, e.g., about 10, 25, 50, 100, 200, 300 or 400 mg per unit dosage.

The compounds can be administered by a variety of routes including oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

For an oral administration form, the compound can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, cornstarch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may additionally contain other pharmaceutical auxiliaries such as surfactants, emulsifiers and stabilizers as well as a propellant.

For subcutaneous or intravenous administration, the compounds, if desired with the substances customary therefore such as solubilizers, emulsifiers or further auxiliaries are brought into solution, suspension, or emulsion. The compounds may also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds of formula I with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethyl methacrylate)); carboxypolymethylene (for example Carbopol™); carbomer; polyvinyl pyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethyl cellulose (HMC), hydroxyethylcellulose (HEC), hydroxypropylcellulose (HPC), methylcellulose (MC), ethylcellulose (EC), carboxyethylcellulose (CEC), ethylhydroxy ethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers.

Certain of the above-mentioned polymers may further be crosslinked by way of standard techniques. The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein delivery systems. Proteins can be entrapped in the poly(lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One can attach poly(ethylene glycol) to proteins (PEGylation) to increase the in vivo half-life of circulating therapeutic proteins and decrease the chance of an immune response.

The present disclosure will now be described with reference to the following non-limiting Examples.

EXPERIMENTAL PROCEDURE

The present disclosure will now be described in more detail with reference to the following non-limiting examples. It should be noted that particular assays used in the examples section are designed to provide an indication of activity. There are many other assays available to determine the activity of given compounds and a result in any one particular assay is therefore not determinative Synthetic Procedures The general syntheses for these scaffolds are shown below (Scheme 1 and Scheme 2). The three rings are referred to as ring A (on the right), ring B (at the top), and ring C (on the left), with each ring being optionally and independently substituted.

Scheme 1

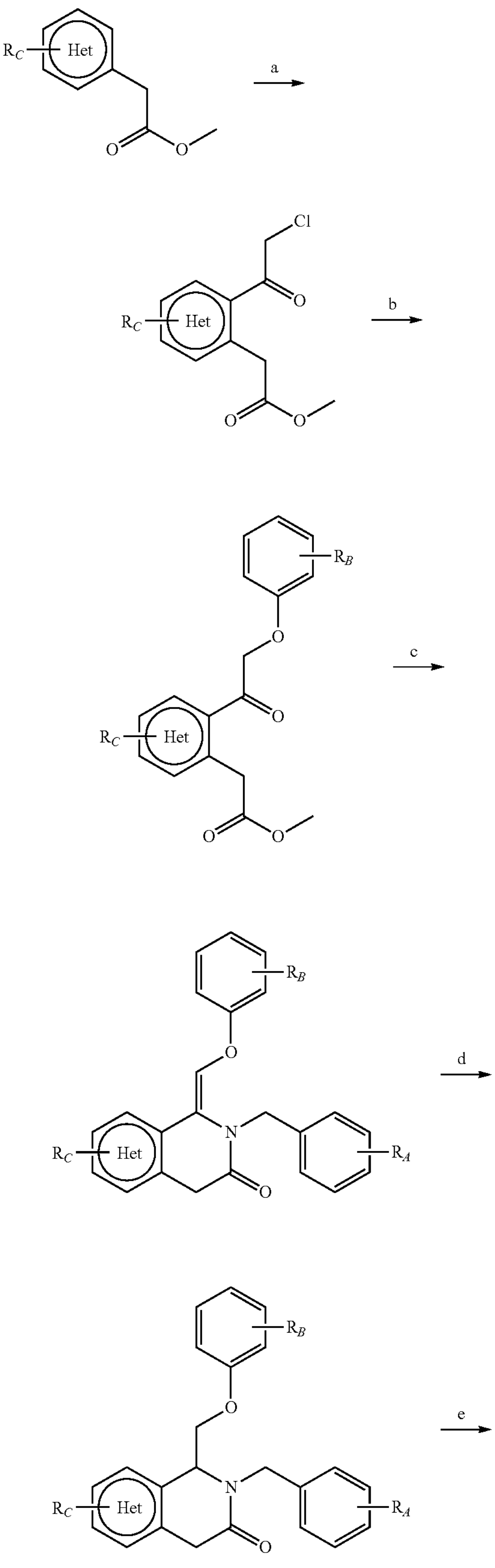

-continued

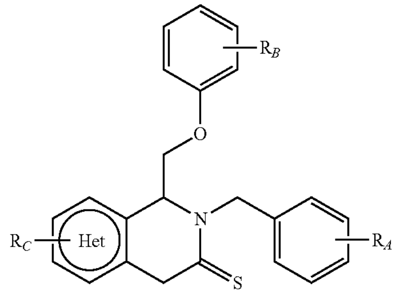

a) chloroacetyl chloride, $AlCl_3$, DCM, 0° C., 1 h; b) substituted phenol, $Cs_2CO_3$, ACN, rt, overnight; c) primary amine, $Ti(i\text{-}PrOH)_4$, $NaBH(OAc)_4$, DCE, 120° C., 30 m, μm; d) Pd/C, $H_2$ (1 atm), EtOH, 1 h; e) Lawesson's Reagent, PhMe, 150° C., μm, 30 m.

-continued

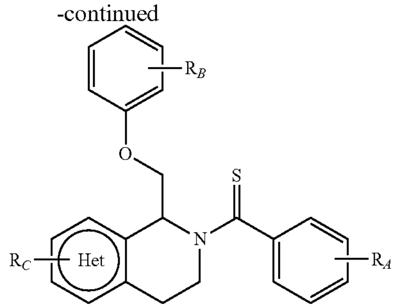

a) cat. butylamine, cat. AcOH, 4 Å MS, $MeNO_2$, reflux, 30 m; b) $LiAlH_4/H_2SO_4$, THF, 0° C. to reflux, 5 m; c) chloroacetyl chloride, $Et_3N$, DCM, 0° C., 1 h; d) substituted phenol, $Cs_2CO_3$, ACN, rt, overnight; e) 1) $POCl_3$, PhMe, reflux, 2 h; 2) $NaBH_4$, MeOH, 0° C., 10 m; f) acid chloride, $Et_3N$, DCM, 1 h OR carboxylic acid, EDCI, DMAP, DCM, rt, overnight g) Lawesson's Reagent, PhMe, 150° C., μm, 30 m.

Scheme 2

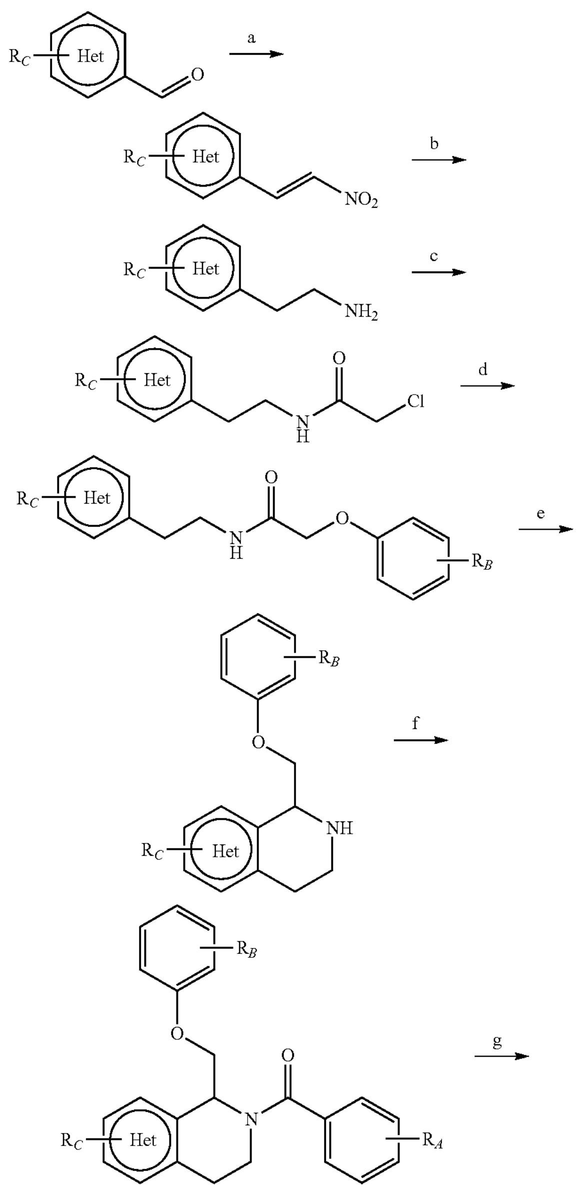

All intermediates in Scheme 2 are prepared according to a literature procedure (Santangelo Freel et al., Synthesis and structure activity relationship of tetrahydroisoquinoline-based potentiators of GluN2C and GluN2D containing N-methyl-D-aspartate receptors. *J. Med. Chem.* 2013, 56, 5351-5381). Ethyl amines in Scheme 2 are either purchased from commercial sources or synthesized from the corresponding aldehyde as outlined in the experimental section.

General Procedure for Nitro Alkenes (Procedure I): Aldehyde (1 eq.) was dissolved in dry nitromethane (~1 M) and butylamine (0.12 eq.), acetic acid (0.2 eq.) and 4 Å molecular sieves (MS) (~10 wt %) were added. The solution was brought to reflux for 30 minutes before the mixture was concentrated in vacuo and the crude material was purified directly via flash column chromatography to afford the title compound.

General Procedure for Ethylamines (Procedure II): Sulfuric acid (2.23 eq.) was added dropwise to a solution of lithium aluminum hydride (4.46 eq.) in THF (~0.15 M) at 0° C. and allowed to stir for 20 min. Nitroalkene (1 eq.), dissolved in dry THF (~1.5 M), was then added dropwise at 0° C. and was allowed to stir for 10 minutes. The mixture was then heated to reflux for 5 minutes, cooled to 0° C., and quenched carefully with iPrOH (6 eq.) and NaOH (9 eq.). The resulting suspension was then filtered and concentrated in vacuo to afford the title compound.

General Procedure for Alpha-Chloro Amides (Procedure III): Hydrochloride salt or free amine (1 eq.) was dissolved in dry DCM (~0.25 M) and triethylamine (2 eq.) was added. The solution was brought to 0° C., 2-chloroacetyl chloride (1.2 eq.) was added, and the mixture was allowed to react at room temperature for 1 hour, when deemed complete by TLC. The reaction was then quenched with 1 M HCl, extracted into DCM, washed with brine (3×), dried over $MgSO_4$, and concentrated in vacuo. The crude product was purified via flash column chromatography to afford the title compound.

General Procedure for Biaryl Linear Compounds (Procedure IV): Phenol (1.2 eq.) was dissolved in acetonitrile (~0.33 M) and cesium carbonate (4 eq.) was added. This mixture was stirred at room temperature (rt) for 2 h before alpha-chloro amide (1 eq.) in acetonitrile (~0.33 M) was added and allowed to react at rt overnight. The reaction was then quenched with saturated ammonium chloride and the product extracted into EtOAc, washed with brine (3×), dried over $MgSO_4$, and concentrated in vacuo. The crude product was purified via flash column chromatography to afford the title compound.

General Procedure for Bischler-Napieralksi Cyclizations (Procedure V): Acetamide (1 eq.) was dissolved in dry ACN (~0.05 M), phosphoryl trichloride (3 eq.) was added and the mixture was heated to reflux. This was allowed to react at reflux overnight when the reaction was deemed complete via LCMS. The reaction was allowed to cool to rt and concentrated in vacuo to afford the crude compound. The crude imine was dissolved in dry MeOH and cooled to 0° C. before sodium borohydride (3 eq.) was added in ~100 mg portions. The mixture was allowed to stir at rt for 10 minutes. The reaction was then concentrated and subsequently partitioned between EtOAc and $H_2O$. The product was then extracted into EtOAc, washed with brine (3×), dried over $MgSO_4$, and concentrated in vacuo. The crude product was purified via flash column chromatography to afford the title compound.

General Procedure for Final CIQ Compounds (Procedure VI-A): Free amine (1 eq.) was dissolved in dry DCM (~0.064 M) and triethylamine (2 eq.) was added followed by acid chloride (1.2 eq.). The mixture was allowed to stir at rt for 1 hour. The reaction was then quenched with 1 M HCl and the organic layer was extracted into DCM, washed with brine (3×), dried over $MgSO_4$, and concentrated in vacuo. The crude product was purified via flash column chromatography to afford the title compound.

General Procedure for Final CIQ Compounds (Procedure VI-B): Carboxylic acid (1.1 eq.) was dissolved in dry DCM (~0.2 M) and cooled to 0° C. EDCI (1.2 eq.) and DMAP (1.2 eq.) were then added and allowed to stir for 2 hours before the free amine (1 eq.) was added and the mixture warmed to rt overnight. The reaction was then quenched with deionized water and the organic layer was extracted into DCM, washed with brine (3×), dried over $MgSO_4$, and concentrated in vacuo. The crude product was purified via flash column chromatography to afford the title compound.

General Procedure for Alpha-Chloro Ketones (Procedure VII): Methyl ester (1 eq.) was dissolved in DCM (~0.5 M) and cooled to 0° C. Aluminum trichloride (1.1 eq.) was added followed by 2-chloroacetyl chloride (1.1 eq.) and the mixture warmed to rt over 1 hour. Upon completion, the reaction was poured over cold water and extracted with DCM, washed with saturated 1 M NaOH (2×), brine, dried over $MgSO_4$, and concentrated in vacuo. The crude product was purified via flash column chromatography to afford the title compound.

General Procedure for Biaryl Ketones (Procedure VIII): To a suspension of potassium iodide (1.2 eq.) and potassium carbonate (2 eq.) in acetone (~0.3 M) was added alpha-chloro ketone (1 eq.) and phenol (1.2 eq.). The resulting mixture was then stirred at rt overnight. Upon completion, the solvent removed in vacuo. The resulting residue was then dissolved in EtOAc and washed with water. The organic layer was then extracted with EtOAc, dried over $MgSO_4$, and concentrated in vacuo. The crude product was purified via flash column chromatography to afford the title compound.

General Procedure for Tertiary Olefins (Procedure IX): An appropriate microwave vial was charged with ketone (1 eq.), primary amine (1.2 eq.), tetraisopropoxytitanium (3 eq.), and DCE (~0.2 M) and the solution was allowed to stir for 10 minutes before sodium triacetoxyborohydride (3 eq.) was added and the mixture was irradiated at 120° C. for 30 min. Upon completion, the reaction was cooled to rt, diluted with DCM and washed with 1 M HCl. The organic layer was extracted with DCM, washed with $NaHCO_3$, washed with brine (3×), dried over $MgSO_4$, and concentrated in vacuo. The crude product was purified via flash column chromatography to afford the title compound as a mixture of E/Z isomers, the mass confirmed via LCMS, and carried forward without further characterization.

General Procedure for Final Pyrrolopyrazinone Compounds (Procedure X-A): A 10 mL microwave vial was charged with olefin (1 eq.), platinum (IV) oxide (10 mol %), and EtOAC (~0.2 M). The vial was then purged with hydrogen and evacuated (3×) and allowed to react at rt under hydrogen for 6-24 hours, monitoring via LCMS to ensure no dehalogenation occurred. Upon first sight of dehalogenation via LCMS, the reaction was diluted with MeOH, filtered through a plug of celite washing with MeOH, and concentrated in vacuo. The crude product was purified via flash column chromatography to afford the title compound.

General Procedure for Final Pyrrolopyrazinone Compounds (Procedure X-B): Olefin (1 eq.) was dissolved in EtOAc (~0.2 M) and 10% Pd/C (0.15 eq.) was added and the mixture was hydrogenated at 1 atm overnight. The reaction mixture was filtered through a pad of celite, washed with methanol, and concentrated in vacuo. The crude product was purified via flash column chromatography to afford the title compound.

General Procedure for Thioamides (Procedure A7): Amide (1 eq.) in a microwave vial was dissolved in toluene (~0.06 M) and Lawesson's Reagent (1.5 eq.) was added. This mixture was allowed to react in a microwave at 150° C. for 30 minutes. The reaction was then diluted with DCM, washed with saturated $NaHCO_3$, water, and brine, dried over $MgSO_4$, and concentrated in vacuo. The crude product was purified via flash column chromatography to afford the title compound.

(3-Chlorophenyl)(7-((4-methoxyphenoxy)methyl)-4,7-dihydrothieno[2,3-c]pyridin-6(5H)-yl)methanone (400)

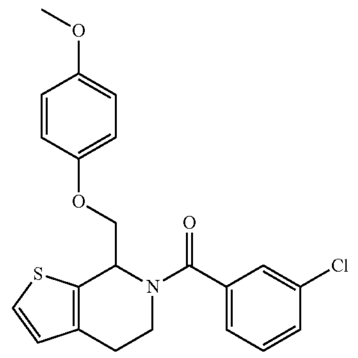 [SMILES: COc1ccc(OCC2c3sccc3CCN2C(=O)c2cccc(Cl)c2)cc1]

General procedure VI-A was followed using 7-((4-methoxyphenoxy)methyl)-4,5,6,7-tetrahydrothieno[2,3-c]pyridine (100 mg, 0.363 mmol), triethylamine (101 μL, 0.726 mmol) and 3-chlorobenzoyl chloride (56 μL, 0.44 mmol) in DCM (5.7 mL). The crude product was purified via flash column chromatography (ISCO, Redisep 4 g column, 0-50% EtOAc/hexanes gradient) to afford the title compound as rotamers in solution and a white foam. (50 mg, 33%). $R_f$ (1:1 EtOAc:Hex): 0.69; HRMS calcd. for $C_{22}H_{21}O_3NClS$, 414.09252 $[M+H]^+$; found 414.09298 $[M+H]^+$.

(3-Chlorophenyl)(4-((4-methoxyphenoxy)methyl)-6,7-dihydrothieno[3,2-c]pyridin-5(4H)-yl)methanone (401)

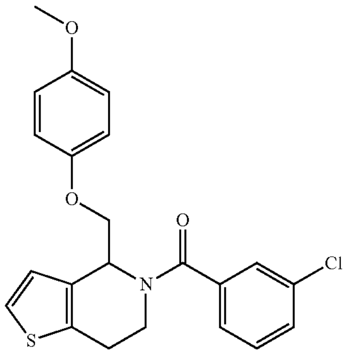 [SMILES: COc1ccc(OCC2c3ccsc3CCN2C(=O)c2cccc(Cl)c2)cc1]

General procedure VI-A was followed using 4-((4-methoxyphenoxy)methyl)-4,5,6,7-tetrahydrothieno[3,2-c]pyridine (50 mg, 0.18 mmol), triethylamine (51 µL, 0.36 mmol) and 3-chlorobenzoyl chloride (28 µL, 0.22 mmol) in DCM (2.8 mL). The crude product was purified via flash column chromatography (ISCO, Redisep 4 g column, 0-70% EtOAc/hexanes gradient) to afford the title compound as rotamers in solution and a white foam. (49 mg, 65%). $R_f$(1:1 EtOAc:Hex): 0.77; HRMS calcd. for $C_{44}H_{40}O_6N_2Cl_2NaS_2$, 849.15970 $[2M+Na]^+$; found 849.16095 $[2M+Na]^+$.

(3-Chlorophenyl)(4-((4-methoxyphenoxy)methyl)-2-methyl-6,7-dihydrothiazolo[5,4-c]pyridin-5(4H)-yl)methanone (402)

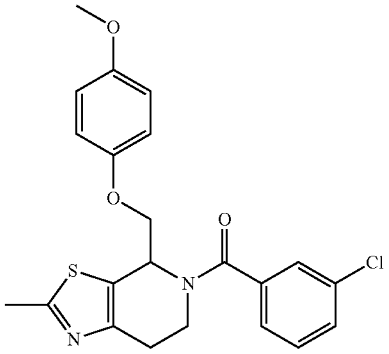 [SMILES: COc1ccc(OCC2c3sc(C)nc3CCN2C(=O)c2cccc(Cl)c2)cc1]

General procedure VI-A was followed using 4-((4-methoxyphenoxy)methyl)-2-methyl-4,5,6,7-tetrahydrothiazolo[5,4-c]pyridine (5.0 mg, 0.014 mmol), triethylamine (3.8 µL, 0.028 mmol) and 3-chlorobenzoyl chloride (2.1 µL, 0.017 mmol) in DCM (0.2 mL). The crude product was purified via flash column chromatography (ISCO, Redisep 4 g column, 0-100% EtOAc/hexanes gradient) to afford the title compound as rotamers in solution and a yellow oil. (5.5 mg, 93%). $R_f$ (1:1 EtOAc:Hex): 0.61; HRMS calcd. for $C_{22}H_{22}O_3N_2ClS$, 429.10342 $[M+H]^+$; found 429.10342 $[M+H]^+$.

(3-Chlorophenyl)(1-((4-methoxyphenoxy)methyl)-3,4-dihydropyrrolo[1,2-a]pyrazin-2(1H)-yl)methanone (420)

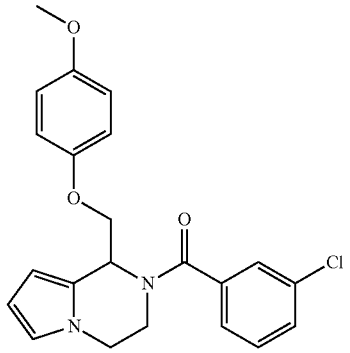 [SMILES: COc1ccc(OCC2c3cccn3CCN2C(=O)c2cccc(Cl)c2)cc1]

General procedure VI-A was followed using 1-((4-methoxyphenoxy)methyl)-1,2,3,4-tetrahydropyrrolo[1,2-a]pyrazine (50 mg, 0.19 mmol), triethylamine (54 µL, 0.39 mmol) and 3-chlorobenzoyl chloride (30 µL, 0.23 mmol) in DCM (3.0 mL). The crude product was purified via flash column chromatography (ISCO, Redisep 4 g column, 0-70% EtOAc/hexanes gradient) to afford the title compound as rotamers in solution and a white foam. (67 mg, 87%). $R_f$(1:1 EtOAc:Hex): 0.58; HRMS calcd. for $C_{22}H_{22}O_3N_2Cl$, 397.13135 $[M+H]^+$; found 397.13144 $[M+H]^+$.

(3-Chlorophenyl)(7-((4-methoxyphenoxy)methyl)-4,7-dihydrofuro[2,3-c]pyridin-6(5H)-yl)methanone (403)

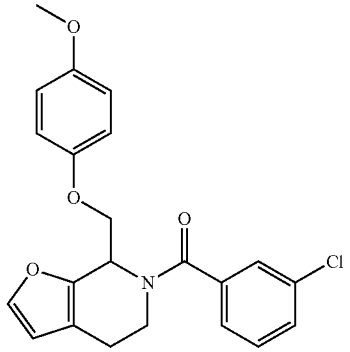 [SMILES: COc1ccc(OCC2c3occc3CCN2C(=O)c2cccc(Cl)c2)cc1]

General procedure VI-A was followed using 7-((4-methoxyphenoxy)methyl)-4,5,6,7-tetrahydrofuro[2,3-c]pyridine (28 mg, 0.108 mmol), triethylamine (30 µL, 0.21 mmol) and 3-chlorobenzoyl chloride (17 µL, 0.13 mmol) in DCM (1.7 mL). The crude product was purified via flash column chromatography (ISCO, Redisep 4 g column, 0-100% EtOAc/hexanes gradient) to afford the title compound as rotamers in solution and a clear oil (19 mg, 44%). $R_f$(1:1 EtOAc:Hex): 0.44; HRMS calcd. for $C_{22}H_{21}O_4NCl$, 398.11536 $[M+H]^+$; found 398.11536 $[M+H]^+$.

(3-Chlorophenyl)(4-((4-methoxyphenoxy)methyl)-1-methyl-1,4,6,7-tetrahydro-5H-pyrazolo[4,3-c]pyridin-5-yl)methanone (407)

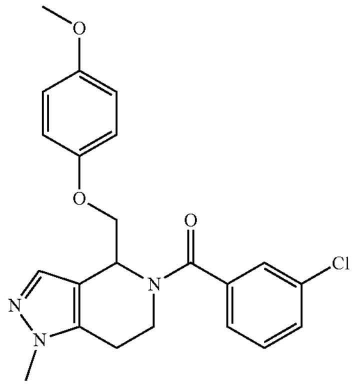 [SMILES: COc1ccc(OCC2c3cnn(C)c3CCN2C(=O)c2cccc(Cl)c2)cc1]

General procedure VI-A was followed using 4-((4-methoxyphenoxy)methyl)-1-methyl-4,5,6,7-tetrahydro-1H-pyrazolo[4,3-c]pyridine (49 mg, 0.18 mmol), triethylamine (50 μL, 0.36 mmol) and 3-chlorobenzoyl chloride (28 μL, 0.38 mmol) in DCM (2.8 mL). The crude product was purified via flash column chromatography (ISCO, Redisep 4 g column, 0-100% EtOAc/hexanes gradient) to afford the title compound as rotamers in solution and a white solid. (71 mg, 96%). $R_f$ (1:1 EtOAc:Hex): 0.64; HRMS calcd. for $C_{22}H_{23}O_3N_3Cl$, 412.14225 $[M+H]^+$; found 412.14237 $[M+H]^+$.

(3-Chlorophenyl)(4-((4-methoxyphenoxy)methyl)-6,7-dihydroisothiazolo[4,5-c]pyridin-5(4H)-yl)methanone (411)

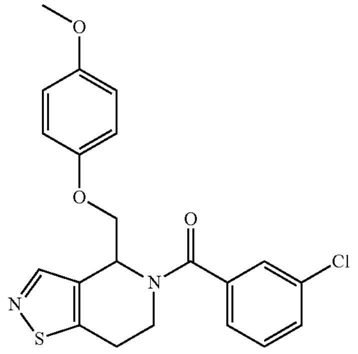 [SMILES: COc1ccc(OCC2c3cnsc3CCN2C(=O)c2cccc(Cl)c2)cc1]

General procedure VI-A was followed using 4-((4-methoxyphenoxy)methyl)-4,5,6,7-tetrahydroisothiazolo[4,5-c]pyridine (45 mg, 0.16 mmol), triethylamine (45 μL, 0.33 mmol) and 3-chlorobenzoyl chloride (25 μL, 0.34 mmol) in DCM (2.5 mL). The crude product was purified via flash column chromatography (ISCO, Redisep 4 g column, 0-100% EtOAc/hexanes gradient) to afford the title compound as rotamers in solution and a yellow oil. (5 mg, 7% over three steps). $R_f$ (1:1 EtOAc:Hex): 0.46; HRMS calcd. for $C_{21}H_{20}O_3N_2ClS$, 415.08777 $[M+H]^+$; found 415.08761 $[M+H]^+$.

(3-Chlorophenyl)(4-((4-methoxyphenoxy)methyl)-6,7-dihydrothieno[3,2-c]pyridin-5(4H)-yl)methanethione (414)

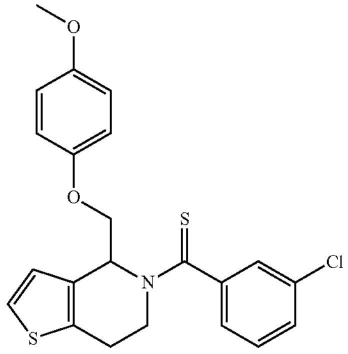

General procedure XI was followed using compound 401 (48 mg, 0.116 mmol) and Lawesson's Reagent (80 mg, 0.20 mmol) in toluene (1.5 mL). The crude product was purified via flash column chromatography (ISCO, Redisep 4 g column, 0-40% EtOAc/hexanes gradient) to afford the title compound as a clear oil. (11 mg, 18%). $R_f$(1:1 EtOAc:Hex): 0.77; HRMS calcd. for $C_{25}H_{25}O_3NClS$, 454.12382 $[M+H]^+$; found 454.12380 $[M+H]^+$.

(3-Chlorophenyl)(4-((4-methoxyphenoxy)methyl)-1-methyl-1,4,6,7-tetrahydro-5H-pyrazolo[4,3-c]pyridin-5-yl)methanethione (413)

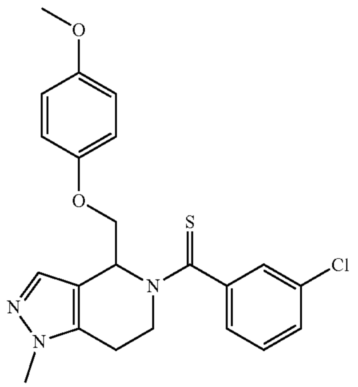

General procedure XI was followed using compound 407 (68 mg, 0.17 mmol) and Lawesson's Reagent (100 mg, 0.25 mmol) in toluene (1.7 mL). The crude product was purified via flash column chromatography (ISCO, Redisep 4 g column, 0-100% EtOAc/hexanes gradient) to afford the title compound as a yellow oil. (42 mg, 59%). $R_f$ (1:1 EtOAc: Hex): 0.44; HRMS calcd. for $C_{22}H_{23}O_2N_3ClS$, 428.11940 $[M+H]^+$; found 428.12005 $[M+H]^+$.

(5-Chlorothiophen-2-yl)(7-((4-methoxyphenoxy)methyl)-4,7-dihydrothieno[2,3-c]pyridin-6(5H)-yl)methanone (404)

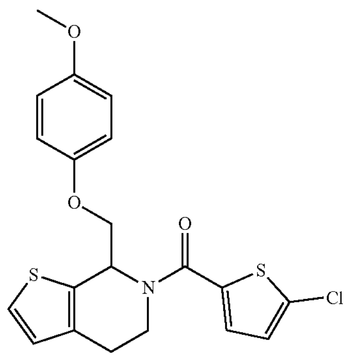 [SMILES: COc1ccc(OCC2c3sccc3CCN2C(=O)c2ccc(Cl)s2)cc1]

General procedure VI-B was followed using 7-((4-methoxyphenoxy)methyl)-4,5,6,7-tetrahydrothieno[2,3-c]pyridine (25 mg, 0.091 mmol), EDCI (17 mg, 0.11 mmol), DMAP (13 mg, 0.11 mmol) and 5-chlorothiophene-2-carboxylic acid (16 mg, 0.10 mmol) in DCM (0.4 mL). The crude product was purified via flash column chromatography (ISCO, Redisep 4 g column, 0-70% EtOAc/hexanes gradient) to afford the title compound as rotamers in solution and a clear oil. (10 mg, 26%). $R_f$ (1:1 EtOAc:Hex): 0.90; HRMS calcd. for $C_{20}H_{19}O_3NClS_2$, 420.04894 $[M+H]^+$; found 420.04910 $[M+H]^+$.

(E)-4,4,4-trifluoro-1-(7-((4-methoxyphenoxy)methyl)-4,7-dihydrothieno[2,3-c]pyridin-6(5H)-yl)but-2-en-1-one (405)

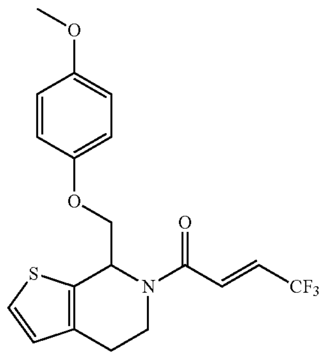 [SMILES: COc1ccc(OCC2c3sccc3CCN2C(=O)/C=C/C(F)(F)F)cc1]

General procedure VI-B was followed using 7-((4-methoxyphenoxy)methyl)-4,5,6,7-tetrahydrothieno[2,3-c]pyridine (25 mg, 0.091 mmol), EDCI (17 mg, 0.11 mmol), DMAP (13 mg, 0.11 mmol) and (E)-4,4,4-trifluorobut-2-enoic acid (14 mg, 0.10 mmol) in DCM (0.4 mL). The crude product was purified via flash column chromatography (ISCO, Redisep 4 g column, 0-70% EtOAc/hexanes gradient) to afford the title compound as rotamers in solution and a yellow oil. (12 mg, 33%). $R_f$ (1:1 EtOAc:Hex): 0.71; HRMS calcd. for $C_{19}H_{19}O_3NF_3S$, 398.10323 $[M+H]^+$; found 398.10325 $[M+H]^+$.

(3-Chlorophenyl)(2-methoxy-4-((4-methoxyphenoxy)methyl)-6,7-dihydrothieno[3,2-c]pyridin-5(4H)-yl)methanone (423)

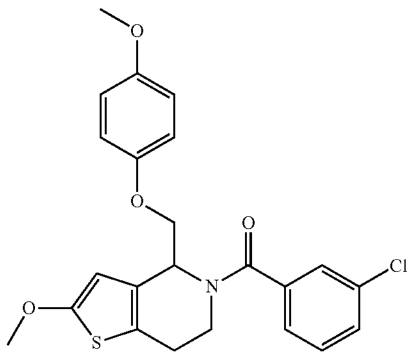 [SMILES: COc1ccc(OCC2c3cc(OC)sc3CCN2C(=O)c2cccc(Cl)c2)cc1]

General procedure VI-A was followed using 2-methoxy-4-((4-methoxyphenoxy)methyl)-4,5,6,7-tetrahydrothieno[3,2-c]pyridine (25 mg, 0.080 mmol), triethylamine (23 μL, 0.16 mmol) and 3-chlorobenzoyl chloride (13 μL, 0.10 mmol) in DCM (1.3 mL). The crude product was purified via flash column chromatography (ISCO, Redisep 4 g column, 0-100% EtOAc/hexanes gradient) to afford the title compound as rotamers in solution and a white foam. (13 mg, 36%). $R_f$ (1:1 EtOAc:Hex): 0.72; HRMS calcd. for $C_{23}H_{23}O_4NClS$, 444.10308 $[M+H]^+$; found 444.10290 $[M+H]^+$.

(1-((4-methoxyphenoxy)methyl)-3,4-dihydropyrrolo[1,2-a]pyrazin-2(1H)-yl)(3-(trifluoromethyl)phenyl)methanone (450)

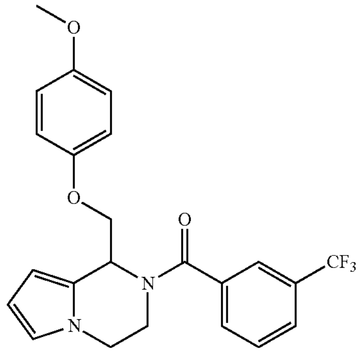 [SMILES: COc1ccc(OCC2c3cccn3CCN2C(=O)c2cccc(C(F)(F)F)c2)cc1]

General procedure VI-A was followed using compound 1-((4-methoxyphenoxy)methyl)-1,2,3,4-tetrahydropyrrolo[1,2-a]pyrazine (100 mg, 0.387 mmol), triethylamine (108 μL, 0.774 mmol) and 3-chlorobenzoyl chloride (70 μL, 0.46 mmol) in DCM (6.5 mL). The crude product was purified via flash column chromatography (ISCO, Redisep 4 g column, 0-70% EtOAc/hexanes gradient) to afford the title compound as rotamers in solution and a white foam. (104 mg, 62%). $R_f$ (1:1 EtOAc:Hex): 0.60; $^1H$ NMR (600 MHz, Chloroform-d, probe temp: −25° C.) δ 8.01 (bs, 0.7H), 7.80 (d, J=7.2 Hz, 0.7H), 7.72 (d, J=7.6 Hz, 1H), 7.65 (s, 0.3H), 7.63-7.54 (m, 1.3H), 6.89-6.75 (m, 4H), 6.74-6.70 (m, 0.7H), 6.66 (m, 0.3H), 6.28-6.17 (m, 1H), 6.14 (d, J=3.3 Hz, 0.3H), 5.95 (d, J=2.5 Hz, 0.7H), 5.42 (dd, J=10.4, 3.8 Hz, 0.7H), 5.00 (dd, J=13.7, 4.0 Hz, 0.7H), 4.43 (dd, J=9.9, 4.2 Hz, 0.3H), 4.34-4.29 (m, 0.3H), 4.23-4.09 (m, 2H), 4.06-3.95 (m, 1H), 3.89 (dd, J=10.1, 4.0 Hz, 1H), 3.77 (s, 3H), 3.50 (td, J=13.5, 4.1 Hz, 1H). $^{13}$C NMR (151 MHz, cdcl3) δ 170.77, 169.52, 153.86, 153.74, 152.48, 151.79, 136.26, 135.97, 131.18, 130.81, 130.59, 130.01, 129.58, 129.10, 126.85, 125.14, 124.66, 124.56, 123.78, 123.01, 122.86, 120.31, 119.54, 115.35, 114.75, 114.50, 114.40, 108.88, 108.61, 105.10, 104.89, 70.24, 68.61, 55.70, 54.33, 49.54, 44.92, 44.27, 43.54, 35.85. HRMS calcd. for $C_{23}H_{22}O_3N_2F_3$, 431.15770 [M+H]$^+$; found 431.15762 [M+H]$^+$. Purity was established using an Agilent pump on a Zorbax XBD-C18 column (4.6 mm×50 mm, 3.5 μm). Method 1: 75-95% MeOH in water over 3 min at 1 mL/min (retention time=1.90 min). Method 2: 95% MeOH in water over 3 min at 1 mL/min (retention time 0.90 min).

Methyl 2-(2-(2-chloroacetyl)-1H-pyrrol-1-yl)acetate

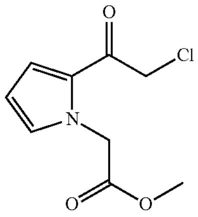

General procedure VII was followed using methyl 2-(1H-pyrrol-1-yl)acetate (2.00 g, 14.4 mmol), aluminum trichloride (2.11 g, 15.8 mmol), and chloroacetyl chloride (1.27 mL, 15.8 mmol) in DCM (29 mL). The crude product was purified via flash column chromatography (ISCO, Redisep 40 g column, 0-100% EtOAc/hexanes gradient) to afford the title compound as a white solid. (0.69 g, 22%). $R_f$ (1:1 EtOAc:Hex): 0.60; HRMS calcd. for $C_9H_{11}O_3NCl$, 216.04220 [M+H]$^+$; found 216.04225 [M+H]$^+$.

Methyl 2-(2-(2-(4-methoxyphenoxy)acetyl)-1H-pyrrol-1-yl)acetate

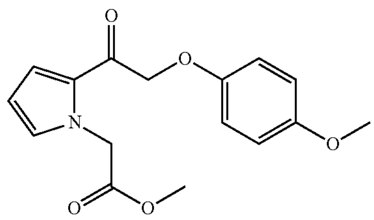 [SMILES: COC(=O)Cn1cccc1C(=O)COc1ccc(OC)cc1]

General procedure VIII was followed using methyl 2-(2-(2-chloroacetyl)-1H-pyrrol-1-yl)acetate (0.61 g, 2.83 mmol), cesium carbonate (1.84 g, 5.66 mmol), potassium iodide (0.56 g, 3.39 mmol) and 4-methoxyphenol (0.42 g, 3.39 mmol) in acetone (9.4 mL). The crude product was purified via flash column chromatography (ISCO, Redisep 24 g column, 0-70% EtOAc/hexanes gradient) to afford the title compound as a white solid. (0.45 g, 52%). $R_f$ (1:1 EtOAc:Hex): 0.76; HRMS calcd. for $C_{16}H_{18}O_5N$, 304.11795 [M+H]$^+$; found 304.11780 [M+H]$^+$.

1-((4-Methoxyphenoxy)methylene)-2-(3-(trifluoromethyl)benzyl)-1,2-dihydropyrrolo[1,2-a]pyrazin-3(4H)-one

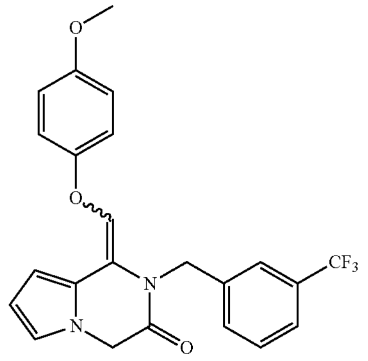 [SMILES: COc1ccc(OC=C2c3cccn3CC(=O)N2Cc2cccc(C(F)(F)F)c2)cc1]

General procedure IX was followed using methyl 2-(2-(2-(4-methoxyphenoxy)acetyl)-1H-pyrrol-1-yl)acetate (200 mg, 0.66 mmol), 3-(trifluoromethyl)benzylamine (0.11 mL, 0.79 mmol), tetraisopropoxytitanium (0.58 mL, 1.98 mmol) and sodium triacetoxyborohydride (419 mg, 1.98 mmol) in DCE (4.0 mL). The crude product was purified via flash column chromatography (ISCO, Redisep 12 g column, 0-35% EtOAc/hexanes gradient) to afford the title compound as a mixture of E and Z isomer and a white solid. (89 mg, 32%). $R_f$(1:1 EtOAc:Hex): 0.70 and 0.74; HRMS calcd. for $C_{23}H_{20}O_3N_2F_3$, 429.14205 [M+H]$^+$; found 429.14178 [M+H]$^+$.

2-(3-fluorobenzyl)-1-((4-methoxyphenoxy)methylene)-1,2-dihydropyrrolo[1,2-a]pyrazin-3(4H)-one

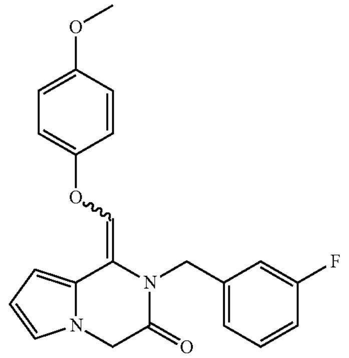 [SMILES: COc1ccc(OC=C2c3cccn3CC(=O)N2Cc2cccc(F)c2)cc1]

General procedure IX was followed using compound methyl 2-(2-(2-(4-methoxyphenoxy)acetyl)-1H-pyrrol-1-yl) acetate (50 mg, 0.16 mmol), 3-fluorobenzylamine (28 μL, 0.20 mmol), tetraisopropoxytitanium (0.15 mL, 0.49 mmol), and sodium triacetoxyborohydride (0.10 g, 0.49 mmol) in DCE (0.8 mL). The crude product was purified via flash column chromatography (ISCO, Redisep 4 g column, 0-35% EtOAc/hexanes gradient) to afford the title compound as a mixture of E/Z isomers and a white solid (24 mg, 38%). HRMS calcd. for $C_{22}H_{20}O_3N_2F$, 379.14525 [M+H]$^+$; found 379.14551 [M+H]$^+$.

1-((4-Methoxyphenoxy)methyl)-2-(3-(trifluoromethyl)benzyl)-1,2-dihydropyrrolo[1,2-a]pyrazin-3(4H)-one (447)

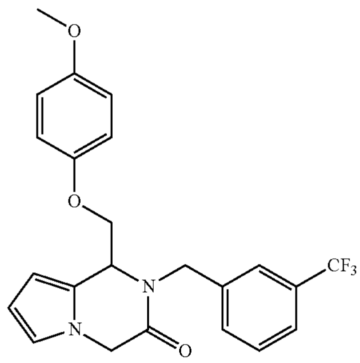 [SMILES: COc1ccc(OCC2c3cccn3CC(=O)N2Cc2cccc(C(F)(F)F)c2)cc1]

General procedure X-B was followed using 1-((4-methoxyphenoxy)methylene)-2-(3-(trifluoromethyl)benzyl)-1,2-dihydropyrrolo[1,2-a]pyrazin-3(4H)-one (55 mg, 0.13 mmol) and Pd/C (14 mg, 0.013 mmol) in EtOAc (0.6 mL). The crude product was purified via flash column chromatography (ISCO, Redisep 4 g column, 0-35% EtOAc/hexanes gradient) to afford the title compound as a white foam. (20 mg, 36%). $R_f$ (1:1 EtOAc:Hex): 0.61; HRMS calcd. for $C_{23}H_{22}O_3N_2F_3$, 431.15770 $[M+H]^+$; found 431.15735 $[M+H]^+$.

2-(3-fluorobenzyl)-1-((4-methoxyphenoxy)methyl)-1,2-dihydropyrrolo[1,2-a]pyrazin-3(4H)-one (1180-453)

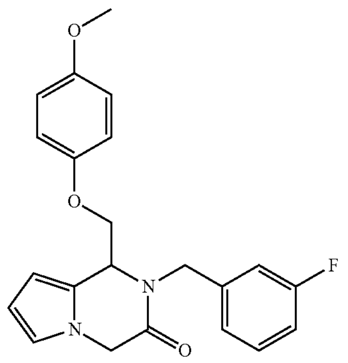 [SMILES: COc1ccc(OCC2c3cccn3CC(=O)N2Cc2cccc(F)c2)cc1]

General procedure X-B was followed using compound 2-(3-fluorobenzyl)-1-((4-methoxyphenoxy)methylene)-1,2-dihydropyrrolo[1,2-a]pyrazin-3(4H)-one (24 mg, 0.063 mmol) and Pd/C (10 mg, 0.010 mmol) in EtOAc (5 mL). The crude product was purified via flash column chromatography (ISCO, Redisep 4 g column, 0-35% EtOAc/hexanes gradient) to afford the title compound as a white solid. (14 mg, 58%). $R_f$ (1:1 EtOAc:Hex): 0.68; $^1$H NMR (400 MHz, Chloroform-d) δ 7.30-7.20 (m, 1H), 7.03 (d, J=7.9 Hz, 1H), 7.00-6.90 (m, 2H), 6.83-6.74 (m, 2H), 6.73-6.65 (m, 2H), 6.64 (dd, J=2.7, 1.6 Hz, 1H), 6.22 (dd, J=3.3, 2.8 Hz, 1H), 5.99 (dd, J=3.5, 1.5 Hz, 1H), 5.43 (d, J=15.4 Hz, 1H), 4.86 (d, J=17.0 Hz, 1H), 4.82 (d, J=3.7 Hz, 2H), 4.75 (d, J=17.0 Hz, 1H), 4.37 (d, J=15.4 Hz, 1H), 4.15 (dd, J=9.7, 3.2 Hz, 1H), 4.02 (dd, J=9.7, 4.5 Hz, 1H), 3.75 (s, 3H). $^{13}$C NMR (101 MHz, Chloroform-d) δ 166.24, 162.98 (d, J=246.9 Hz, $^1$J), 154.34, 152.03, 138.73 (d, J=7.1 Hz, $^3$J), 130.33 (d, J=8.2 Hz, $^3$J), 124.09, 123.48 (d, J=2.9 Hz, 4J), 118.82, 115.60, 114.93 (d, J=21.9 Hz, 2J), 114.93 (d, J=21.2 Hz, 2J), 114.62, 109.46, 103.83, 72.16, 55.68, 54.64, 49.02, 48.23. HRMS calcd. for $C_{22}H_{22}O_3N_2F$, 381.16090 $[M+H]^+$; found 381.16132 $[M+H]^+$. Purity was established using an Agilent pump on a Zorbax XBD-C18 column (4.6 mm×50 mm, 3.5 μm). Method 1: 75-95% MeOH in water over 3 min at 1 mL/min (retention time=1.41 min). Method 2: 85-95% MeOH in water over 5 min at 1 mL/min (retention time 0.80 min).

Separation of 1180-447 Enantiomers

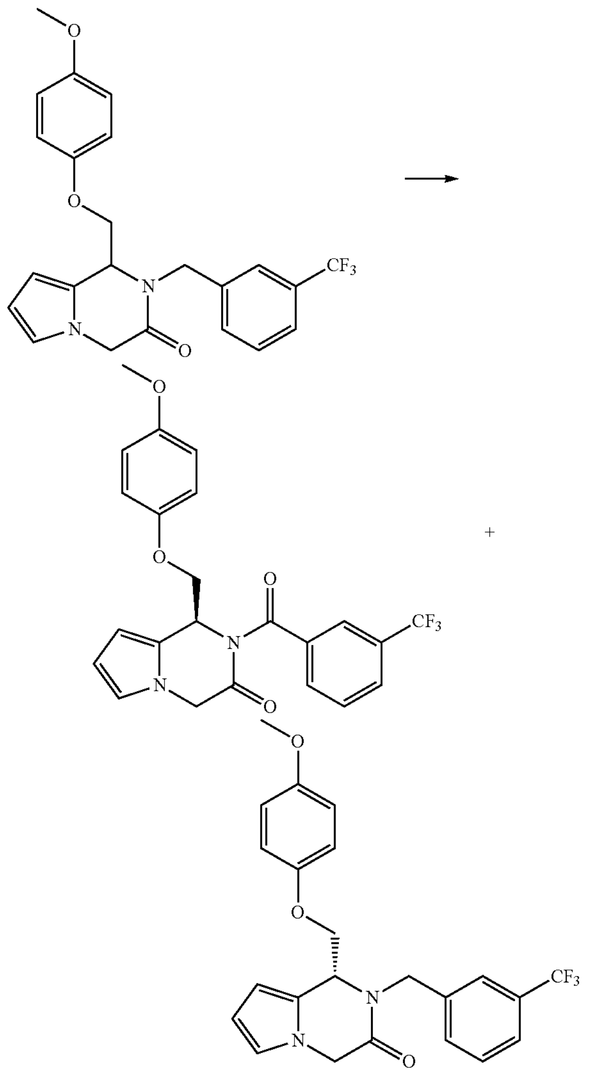

Semipreparative separation of 1180-447 enantiomers from racemic 1180-447 (0.020 g) was done using a ChiralPak AD-H (30 mm×250 mm) with the following conditions: 20 mL/min flow rate, 10 mL injection volume (2 mg/1 mL), 90% hexanes/10% IPA over 60 min to afford S-(−)-1180-447, $t_R$ 33.8 min; R-(+)-1180-447, $t_R$ 47.2 min. The enantiomeric excess (ee) was determined using an Agilent pump on a ChiralPak OD-H column (4.6 mm×150 mm, 5 m) with the following conditions: 1 mL/min flow rate, 10 μL injection volume, 90% hexanes/10% IPA. S-(−)-1180-447: $t_R$ 21.4 min; >99% ee; [α]D20=−45 (c 0.10, dry $CHCl_3$). R-(+)-1180-447: $t_R$ 30.1 min, >99% ee; [α]D20=+45 (c 0.10, dry $CHCl_3$). The proton spectrum for each enantiomer was identical to that of the racemic mixture.

Separation of 1180-450 Enantiomers

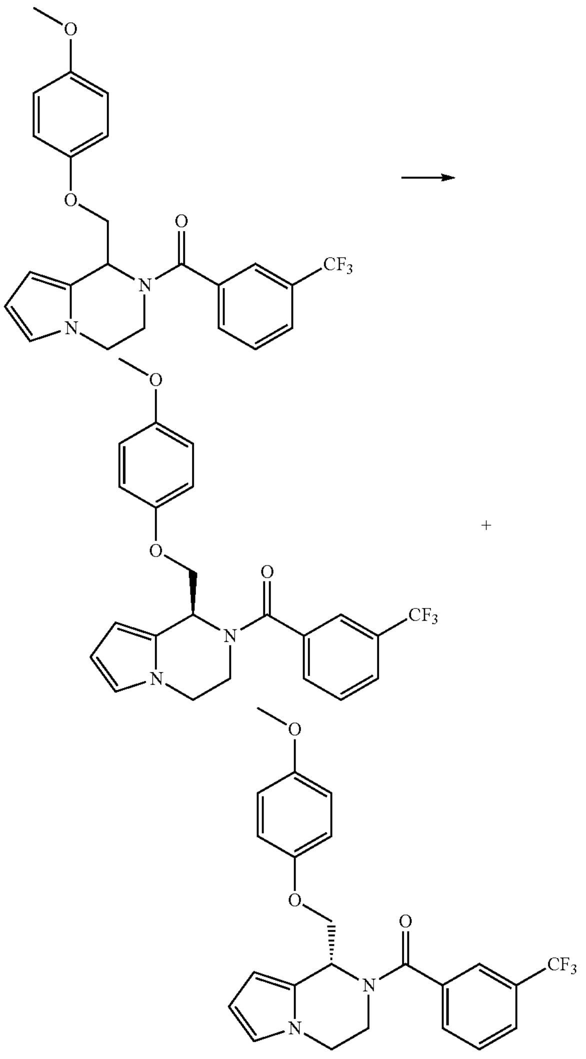

Semipreparative separation of 1180-450 enantiomers from racemic 1180-450 (0.020 g) was done using a ChiralPak AD-H (30 mm×250 mm) with the following conditions: 20 mL/min flow rate, 10 mL injection volume (2 mg/1 mL), 90% hexanes/10% IPA over 60 min to afford R-(+)-1180-450, $t_R$ 41.4 min; S-(−)-1180-450, $t_R$ 50.5 min. The enantiomeric excess (ee) was determined using an Agilent pump on a ChiralPak OD-H column (4.6 mm×150 mm, 5 μm) with the following conditions: 1 mL/min flow rate, 10 μL injection volume, 90% hexanes/10% IPA. R-(+)-1180-450: $t_R$ 27.1 min; >99% ee; [α]D20=+148 (c 0.10, dry $CHCl_3$). S-(−)-1180-450: $t_R$ 32.4 min, >99% ee; [α]D20=−149 (c 0.10, dry $CHCl_3$). The proton spectrum for each enantiomer was identical to that of the racemic mixture.

Synthesized Compounds: Compounds have been synthesized focused on conversion of the phenyl ring C in CIQ to heterocyclic derivatives. Changes to ring A, linker region, and amide carbonyl were explored holding the heterocyclic nature of ring C in place. Efficacy was improved and potency maintained upon ring C conversion to a thiophene as in compounds 1180-400 and 1180-401. Efficacy, potency, and solubility were improved upon conversion of the tetrahydroisoquinoline core to a pyrrolopyrazine core seen in compound 1180-420 (Table 1). Activity was maintained upon replacement of ring A in 1180-400 with a substituted thiophene as in compound 1180-404 (Table 2). Activity was maintained upon substitution with a thiophene as in compound 1180-423 and activity significantly improved into the nanomolar range at GluN2C/D upon conversion of the pyrrolopyrazine core to a pyrrolopyrazinone core and subsequent separation of the enantiomers as in compound R-(+)-1180-447 (Tables 3 and 4). The pyrrole-based compounds (1180-420 and -447) also show an excellent off-target profile against other ion channels (none >50% inhibition) (Table 5) as well as other CNS receptors (>50% inhibition at only 4/44 receptors tested) (Tables 6 and 7). Finally, these compounds are highly brain penetrant showing a roughly 2:1 brain to plasma ratio and max brain concentration of 4 μM with half-lives of greater than 1 hour in plasma (Tables 8 and 9).

In vitro analysis of 1180 series analogs: Protocols utilizing *Xenopus laevis* oocytes were approved by the Emory University Institutional Animal Care and Use Committee. *Xenopus laevis* oocytes were purchased unfertilized from Ecocyte (Austin, Tex.). The oocytes were injected with mRNA to express recombinant rat GluN1/GluN2A, GluN1/GluN2B, GluN1/GluN2C, and GluN1/GluN2D and two-electrode voltage clamp (TEVC) recordings were performed. Drs. S. Heinemann (Salk Institute), S. Nakanishi (Kyoto University), and P. Seeburg (University of Heidelberg) provided the cDNAs for rat GluN1-1a (GenBank accession numbers U11418 and U08261, referred to as GluN1 henceforth), GluN2A (D13211), GluN2B (U11419), GluN2C (M91563), and GluN2D (D13213). GluN2C and GluN2D were altered according to literature precedent. (Monyer, H.; Burnashev, N.; Laurie, D. J.; Sakmann, B.; Seeburg, P. H., Developmental and regional expression in the rat brain and functional properties of four NMDA receptors. *Neuron* 1994, 12, 529-540.) Isolation of oocytes, synthesis of cRNA, and injections of cRNA were each done according to literature precedent.[34] Oocytes were placed in perfusion chamber and continuously washed during TEVC recordings with a solution consisting of the following (in mM): 90 NaCl, 0.5 BaCl, 0.005 EDTA, 1.0 KCl, and 10 HEPES at pH 7.4 and 23° C. Glass electrodes were pulled from thin-walled glass capillaries (tip resistance 0.5-2.5 MΩ) and filled with 0.3-3.0 M KCl while the oocyte membrane potential was held constant at −40 mV via an OC-725C amplifier (Warner Instrument Co.). Each compound was brought up in 20 mM DMSO and diluted with recording solution containing 30 μM glycine and 100 μM glutamate to the target concentration. To prevent the current increase typically seen during experiments with oocytes expressing GluN1/GluN2A receptors, the oocytes were either injected with 20 nL of 100 mM K-BAPTA (potassium 1,2-bis(o-aminophenoxy)ethane-N,N,N,N-tetraacetic acid) or pretreated with 50 μM BAPTA-AM (1,2-bis(o-aminophenoxy)ethane-N,N,N,N-tetraacetic acid tetraacetoxymethyl ester) for 10 minutes. For test compounds with potentiation that exceeded 125% at 30 μM, an $EC_{50}$ value (the half-maximal effective concentration of potentiator) was determined by fitting the following equation $$Response=(100-max)/(1+([concentration]/EC_{50})^{N})+max$$

to the mean composite concentration-response data normalized to the current in the absence of the potentiator (100%) where N equals the Hill slope and max is the maximal response predicted for saturating concentration of potentiator.

Solubility determination: The maximum solubility for compounds CIQ, 1180-400, -420, -447, -450, and -453 was determined using a BMG Labtech Nephelostar nephelometer (Offenburg, Germany) according to manufacturer's instructions. Compound powder (1-3 mg) was taken up in DMSO (Sigma-Aldrich) to a 20 mM stock solution and serially diluted (~10 μL) to 15, 10, 5, 2.5 1.25, and 0.625 μM stock solutions. These, along with a DMSO blank, were distributed in triplicate to black, clear-bottom 96 well plates in 3 μL increments and subsequently diluted 100-fold using the oocyte recording solution described in the section above. Each solution was shaken gently for 30 min before submission to the nephelometer.

In vitro analysis of off-target selectivity for 1180-420 and 1180-447: Receptor binding profiles, $K_i$ determinations, and hERG activity of compounds 1180-420 and 1180-447 were generously provided by the National Institute of Mental Health's Psychoactive Drug Screening Program, Contract # HHSN-271-2013-00017-C(NIMH PDSP). The NIMH PDSP is Directed by Bryan L. Roth at the University of North Carolina at Chapel Hill and Project Officer Jamie Driscoll at NIMH, Bethesda Md., USA. Radioligand binding was measured in the presence of 10 μM 1180-420 and 1180-447. A $K_i$ value was determined for each receptor at which compound 1180-420 and 1180-447 showed >50% inhibition. For experimental details please refer to the PDSP web site https://pdsp.unc.edu/ims/investigator/web/. Both 1180-420 and 1180-447 were also tested at AMPA, nicotinic acetylcholine, serotonin, GABA, and glycine ion channels using a two-electrode voltage clamp assay.

In vivo analysis of 1180-420 and 1180-447 for pharmacokinetic properties: In vivo analysis of 1180-420 and 1180-447 for pharmacokinetic properties was performed by Pharmaron (Irvine, Calif.). A group (15) of fed, male C57BL/6 mice approximately 6-8 weeks of age were injected IP with 10 mg/kg (10 ml/kg injection volume and 1 mg/mL conc. vehicle) of drug using 1:1 PEG400:water as a vehicle. Samples were collected from the blood and brain at 15 min, 30 min, 1 hour, 2 hours, and 4 hours after administration (3 mice per time point) following $CO_2$ anesthesia. Collection from the brain was performed as follows: The mouse is terminally anaesthetized via rising concentration of $CO_2$ and as much blood is removed as possible via cardiac puncture. The cardiac puncture is done by opening the chest cavity to expose the heart, cutting an incision in the right auricle using surgical scissors and finally injecting a saline solution (~10 mL) slowly into the left ventricle via syringe. The mouse is placed head down at a 45-degree angle to facilitate blood removal. After perfusion, the brain ventricle is opened, and the brain is removed. The brain is washed with saline, dried with surgical gauze, placed in tared tubes, and stored at −75° C. before analysis. The mixtures were then vortexed for 30 seconds and subsequently centrifuged (~4000 rpm) for 15 minutes. The supernatant was diluted 3-fold with water and a 2 μL aliquot of the diluted supernatant was injected into an LC-MS/MS system using verapamil as an internal standard.

TABLE 1

Heterocyclic modifications to the core scaffold

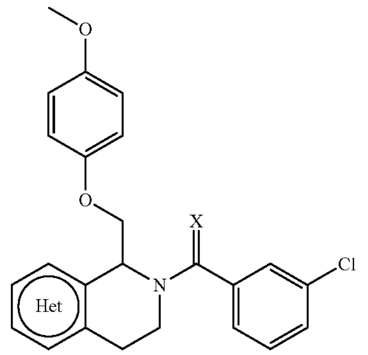

| Compound Number (1180-x) | Het | X | GluN2C $EC_{50}$ (μM)/ Max % | GluN2D $EC_{50}$ (μM)/ Max % |
|---|---|---|---|---|
| 400 | 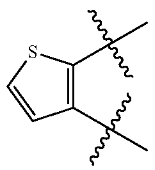 [SMILES: *c1ccsc1*] | O | 3.8/288 | 3.5/391 |
| 401 | 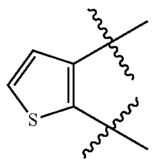 [SMILES: *c1ccsc1*] | O | 3.6/320 | 4.7/369 |
| 402 | 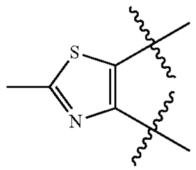 [SMILES: *c1nc(C)sc1*] | O | NE | NE |
| 420 | 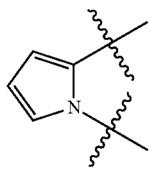 [SMILES: *c1cccn1*] | O | 1.9/312 | 2.3/374 |
| 403 | 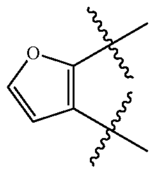 [SMILES: *c1ccoc1*] | O | 7.4/353 | 9.6/527 |
| 407 | 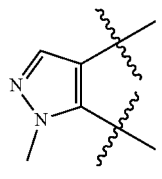 [SMILES: *c1cnn(C)c1*] | O | 207% @ 100 μM | 216% @ 100 μM |

TABLE 1-continued

Heterocyclic modifications to the core scaffold

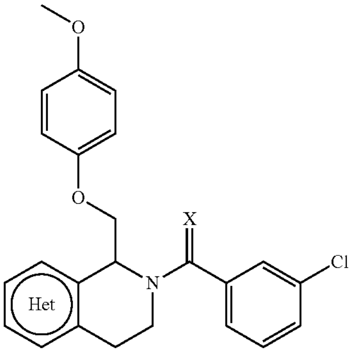

| Compound Number (1180-x) | Het | X | GluN2C $EC_{50}$ (μM)/ Max % | GluN2D $EC_{50}$ (μM)/ Max % |
|---|---|---|---|---|
| 411 | 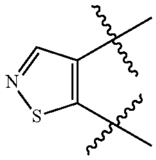 [SMILES: *c1cnsc1*] | O | 11/194 | 15/238 |
| 414 | 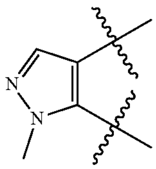 [SMILES: *c1cnn(C)c1*] | S | NE | NE |
| 413 | 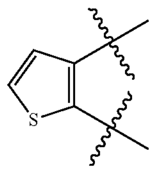 [SMILES: *c1ccsc1*] | S | NE | NE |

NE indicates less than 20% potentiation at 30 μM; No activity was observed at GluN2A or GluN2B for any compound listed

TABLE 2

Replacement of the A-ring with various heterocyclic and alkenyl derivatives

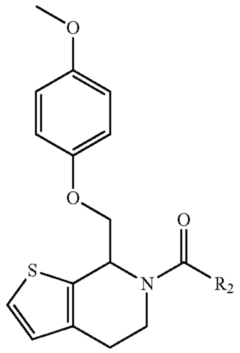

| Compound Number (1180-x) | $R_2$ | GluN2C $EC_{50}$ (μM)/Max % | GluN2D $EC_{50}$ (μM)/Max % |
|---|---|---|---|
| 404 | | 5.1/269 | 7.4/352 |
| 405 | | 13/282 | 13/317 |

NE indicates less than 20% potentiation at 30 μM; No activity was observed at GluN2A or GluN2B for any compound listed

TABLE 3

Pyrrolopyrazine and Pyrrolopyrazinone Derivatives

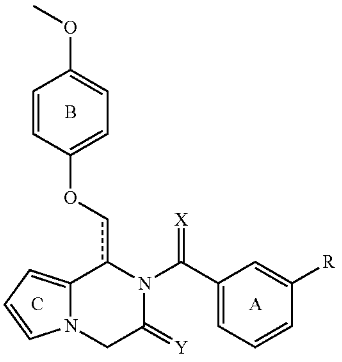

| | | | | $pEC_{50}$ [95% CI] (max) (%) | | Solubility |
|---|---|---|---|---|---|---|
| # | X* | Y* | R | GluN2C | GluN2D | (μM) |
| CIQ (TIQ Core) | | | Cl | 5.3 (233) | 5.3 (215) | 8 |
| 450 | O | — | $CF_3$ | 5.8 [5.7-5.9] (381) | 5.7 [5.5-5.9] (288) | 58 |
| 447 | — | O | $CF_3$ | 5.9 [5.7-6.0] (298) | 5.8 [5.6-6.0] (396) | 57 |
| 453 | — | O | F | 5.5 [5.4-5.6] (348) | 5.5 [5.4-5.6] (334) | 74 |

*where X or Y are a dash (—), there is no heteroatom substituent and this position has two hydrogens individually attached to the adjacent C.

TABLE 4

Pyrrolopyrazine and Pyrrolopyrazinone Derivatives

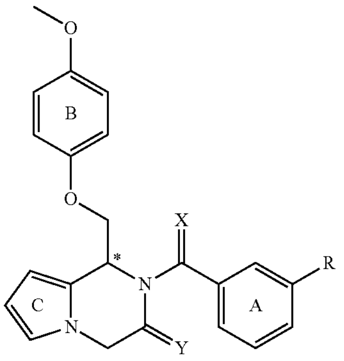

| # | X* | Y* | R | pEC$_{50}$ [95% CI] (max) (%) GluN2C | GluN2D |
|---|---|---|---|---|---|
| S-(−)-447 | — | O | $CF_3$ | ND (84) | ND (88) |
| R-(+)-447 | — | O | $CF_3$ | 6.1 [6.0-6.3] (276) | 6.1 [6.0-6.2] (332) |
| S-(−)-450 | O | — | $CF_3$ | ND (99) | ND (98) |
| R-(+)-450 | O | — | $CF_3$ | 5.9 [5.8-6.0] (464) | 5.9 [5.8-5.9] (542) |

ND = not determined;

*where X or Y are a dash (—), this indicates that there is no heteroatom substituent and this position has two hydrogens individually attached to the adjacent C.

TABLE 5

Off-target actions of 1180-447 and 1180-420 at ligand-gated ion channels demonstrating selectivity for NMDA receptors (no inhibition > 50%).

| Receptor | % control response (10 μM 1180-447)[a] | % control response (10 μM 1180-420)[a] |
|---|---|---|
| GluA1 | 96.8 ± 13.3 | 98.9 ± 13.7 |
| GluA2 | 99.3 ± 2.9 | 101.6 ± 1.3 |
| α4β2-nACh | 52.7 ± 6.3 | 56.4 ± 5.3 |
| α1β2γδ-nACh | 78.5 ± 4.5 | 93.4 ± 15.5 |
| 5-$HT_{3A}$ | 98.1 ± 10.4 | ND |
| α1β2γ2-$GABA_A$ | 81.7 ± 7.5 | 81.4 ± 8.5 |
| α1-Glycine | ND | 77.6 ± 4.9 |

[a]The mean responses to agonist with 10 μM 1180-420 and 1180-447 and the standard error of the mean are given for each compound and receptor tested.

TABLE 6

Off-target actions of compound 1180-447 demonstrating selectivity for NMDA receptors (no $K_i$ > 5.8).

| Receptor | Radioligand binding in 10 μM 1180-447 (% control) | p$K_i$ values from non-linear regression of radioligand competition binding isotherms |
|---|---|---|
| 5-$HT_{1A}$ | 101 | — |
| 5-$HT_{1B}$ | 109 | — |
| 5-$HT_{1D}$ | 115 | — |
| 5-$HT_{1E}$ | 80 | — |
| 5-$HT_{2A}$ | 49 | 5.7 ± 0.1 |
| 5-$HT_{2B}$ | 78 | — |
| 5-$HT_{2C}$ | 32 | <5 |
| 5-$HT_3$ | 68 | — |
| 5-$HT_{5A}$ | 92 | — |
| 5-$HT_6$ | 85 | — |
| 5-$HT_7$ | 83 | — |
| $D_1$ | 87 | — |
| $D_2$ | 101 | — |
| $D_3$ | 93 | — |

TABLE 6-continued

Off-target actions of compound 1180-447 demonstrating selectivity for NMDA receptors (no $K_i$ > 5.8).

| Receptor | Radioligand binding in 10 μM 1180-447 (% control) | p$K_i$ values from non-linear regression of radioligand competition binding isotherms |
|---|---|---|
| $D_4$ | 101 | — |
| $D_5$ | 67 | — |
| serotonin transporter | 91 | — |
| norepinephrine transporter | 70 | — |
| dopamine transporter | 76 | — |
| μ-opioid receptor | 99 | — |
| δ-opioid receptor | 93 | — |
| κ-opioid receptor | 47 | 5.8 ± 0.1 |
| GABAA | 118 | — |
| $H_1$ | 86 | — |
| $H_2$ | 103 | — |
| $H_3$ | 79 | — |
| $H_4$ | 107 | — |
| $\alpha_{1A}$ | 97 | — |
| $\alpha_{1B}$ | 102 | — |
| $\alpha_{1D}$ | 79 | — |
| $\alpha_{2A}$ | 98 | — |
| $\alpha_{2B}$ | 94 | — |
| $\alpha_{2C}$ | 85 | — |
| $\beta_1$ | 80 | — |
| $\beta_3$ | 73 | — |
| $M_1$ | 88 | — |
| $M_2$ | 90 | — |
| $M_3$ | 87 | — |
| $M_4$ | 100 | — |
| $M_5$ | 108 | — |
| benzodiazapine rat brain site | 88 | — |
| translocator protein (peripheral benzodiazepine site) | 84 | — |
| hERG binding | 70 | — |
| $\sigma_1$ | 76 | — |
| $\sigma_2$ | 32 | 5.8 ± 0.1 |

Receptor binding profiles of compound 1180-447 were generously provided by the National Institute of Mental Health's Psychoactive Drug Screening Program, Contract # HHSN-271-2013-00017-C(NIMH PDSP). The NIMH PDSP is directed by Bryan L. Roth at the University of North Carolina at Chapel Hill and Project Officer Jamie Driscoll at NIMH, Bethesda Md., USA. Radioligand binding was measured in the presence of 10 μM 1180-447. A $K_i$ value was determined for each receptor at which compound 1180-447 showed >50% inhibition. For experimental details please refer to the PDSP web site https://pdsp.unc.edu/ims/investigator/web/.

TABLE 7

Off-target actions of compound 1180-420 demonstrating selectivity for NMDA receptors (no $K_i$ > 5.9).

| Receptor | Radioligand binding in 10 μM 1180-420 (% control) | p$K_i$ values from non-linear regression of radioligand competition binding isotherms |
|---|---|---|
| 5-$HT_{1A}$ | 110 | — |
| 5-$HT_{1B}$ | 95 | — |
| 5-$HT_{1D}$ | 112 | — |
| 5-$HT_{1E}$ | 78 | — |
| 5-$HT_{2A}$ | 69 | — |
| 5-$HT_{2B}$ | 97 | — |
| 5-$HT_{2C}$ | 113 | — |
| 5-$HT_3$ | 116 | — |

TABLE 7-continued

Off-target actions of compound 1180-420 demonstrating selectivity for NMDA receptors (no $K_i$ > 5.9).

| Receptor | Radioligand binding in 10 μM 1180-420 (% control) | $pK_i$ values from non-linear regression of radioligand competition binding isotherms |
|---|---|---|
| 5-$HT_{5A}$ | 95 | — |
| 5-$HT_6$ | 75 | — |
| 5-$HT_7$ | 115 | — |
| $D_1$ | 59 | — |
| $D_2$ | 87 | — |
| $D_3$ | 71 | — |
| $D_4$ | 90 | — |
| $D_5$ | 37 | 5.9 ± 0.2 |
| serotonin transporter | 86 | — |
| norepinephrine transporter | 75 | — |
| dopamine transporter | 98 | — |
| μ-opioid receptor | 104 | — |
| δ-opioid receptor | 89 | — |
| κ-opioid receptor | 32 | 5.8 ± 0.1 |
| GABAA | 110 | — |
| $H_1$ | 74 | — |
| $H_2$ | 75 | — |
| $H_3$ | 99 | — |
| $H_4$ | 90 | — |
| $\alpha_{1A}$ | 91 | — |
| $\alpha_{1B}$ | 100 | — |
| $\alpha_{1D}$ | 79 | — |
| $\alpha_{2A}$ | 79 | — |
| $\alpha_{2B}$ | 93 | — |
| $\alpha_{2C}$ | 83 | — |
| $\beta_1$ | 98 | — |
| $\beta_3$ | 74 | — |
| $M_1$ | 90 | — |
| $M_2$ | 110 | — |
| $M_3$ | 69 | — |
| $M_4$ | 84 | — |
| $M_5$ | 101 | — |
| benzodiazapine rat brain site | 71 | — |
| translocator protein (peripheral benzodiazepine site) | 67 | — |
| hERG binding | 73 | — |
| $\sigma_1$ | 76 | — |
| $\sigma_2$ | 48 | 5.8 ± 0.1 |

Receptor binding profiles of compound 1180-420 were generously provided by the National Institute of Mental Health's Psychoactive Drug Screening Program, Contract # HHSN-271-2013-00017-C(NIMH PDSP). The NIMH PDSP is Directed by Bryan L. Roth at the University of North Carolina at Chapel Hill and Project Officer Jamie Driscoll at NIMH, Bethesda Md., USA. Radioligand binding was measured in the presence of 10 μM 1180-420. A $K_i$ value was determined for each receptor at which compound 1180-420 showed >50% inhibition. For experimental details please refer to the PDSP web site https://pdsp.unc.edu/ims/investigator/web/.

TABLE 8

Pharmacokinetic data for compound 1180-447 demonstrating excellent brain penetration (brain:plasma of ~2:1)

Plasma IP 10 mg/kg fed

| ID | $C_{max}$ (ng/mL) | $C_{max}$ (μM) | $t_{max}$ (hr) | $AUC_{LAST}$ (hr · ng/mL) | $AUC_{INF}$ (hr · ng/mL) | $t½_{terminal}$ (hr) | AUC % Extrapolation |
|---|---|---|---|---|---|---|---|
| Mean | 635 | 1.5 | 0.3 | 715 | 760 | 1.0 | 6 |

Brain IP 10 mg/kg fed

| ID | $C_{max}$ (ng/g) | $C_{max}$ (μM) | $t_{max}$ (hr) | $AUC_{LAST}$ (h*ng/g) | $AUC_{INF}$ (h*ng/g) | $t½_{terminal}$ (hr) | AUC % Extrapolation | Ratio_$AUC_{LAST}$ (Brain/plasma) |
|---|---|---|---|---|---|---|---|---|
| Mean | 1668 | 3.9 | 0.5 | 1670 | 1836 | 1.2 | 9 | 2 |

TABLE 9

Pharmacokinetic data for compound 1180-420 demonstrating excellent brain penetration (brain:plasma of ~2:1)

| Plasma IP 10 mg/kg fed | | | | | | | |
|---|---|---|---|---|---|---|---|
| ID | $C_{max}$ (ng/mL) | $C_{max}$ (μM) | $t_{max}$ (hr) | $AUC_{LAST}$ (hr · ng/mL) | $AUC_{INF}$ (hr · ng/mL) | $t½_{terminal}$ (hr) | AUC % Extrap-olation |
| Mean | 841 | 2.1 | 0.3 | 792 | 856 | 1.1 | 8 |

| Brain IP 10 mg/kg fed | | | | | | | | |
|---|---|---|---|---|---|---|---|---|
| ID | $C_{max}$ (ng/g) | $C_{max}$ (μM) | $t_{max}$ (hr) | $AUC_{LAST}$ (h*ng/g) | $AUC_{INF}$ (h*ng/g) | $t½_{terminal}$ (hr) | AUC % Extrap-olation | Ratio_$AUC_{LAST}$ (Brain/ plasma) |
| Mean | 1408 | 3.5 | 0.3 | 1315 | 1413 | 1.1 | 7 | 2 |

What is claimed is:

1. A compound selected from:

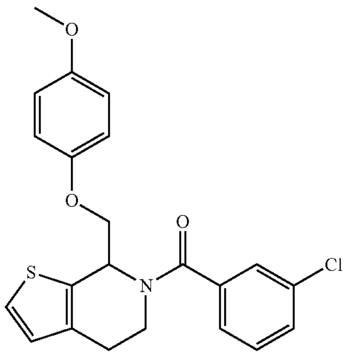

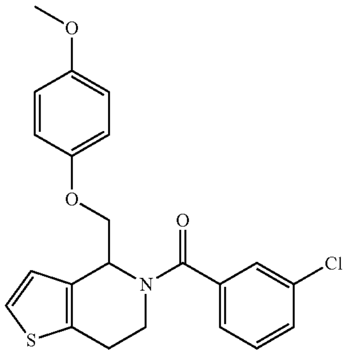

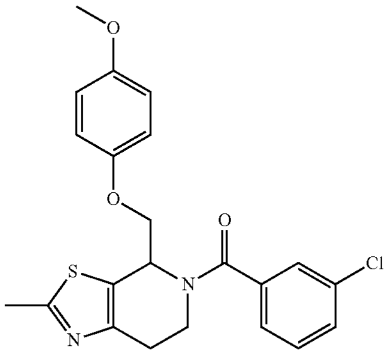

-continued

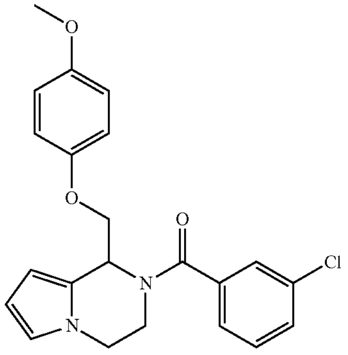

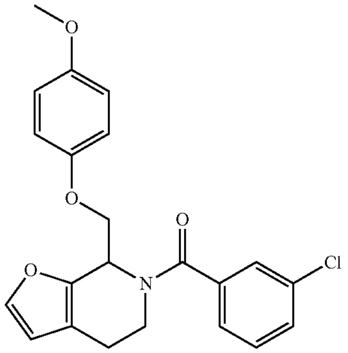

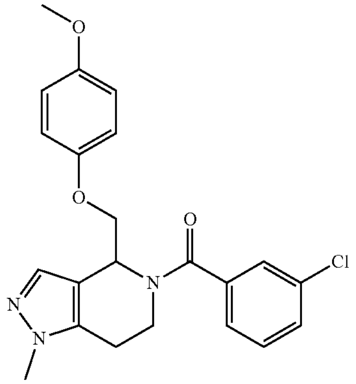

-continued
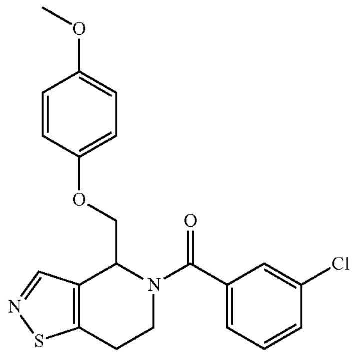
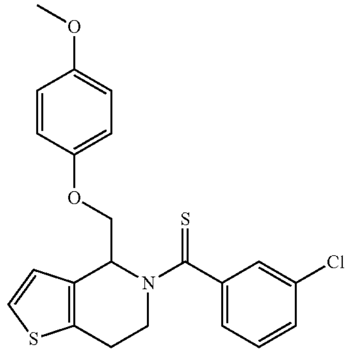
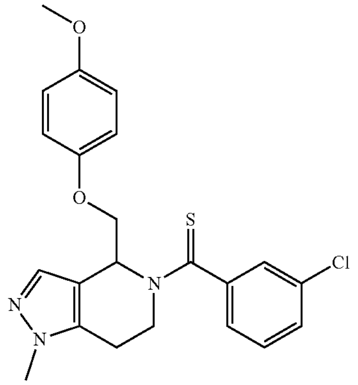
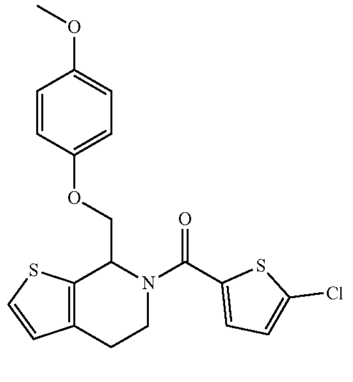
-continued
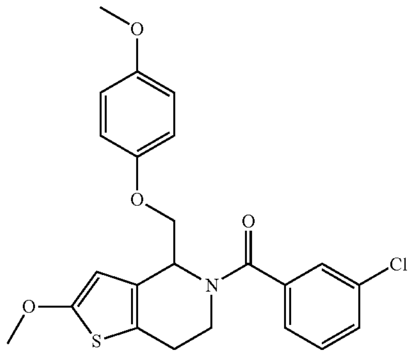
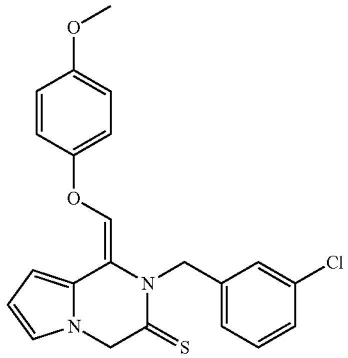
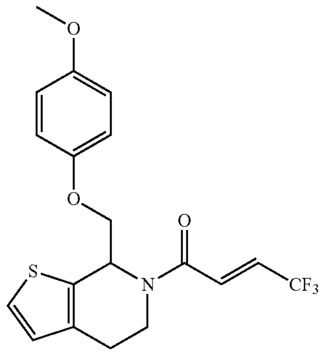
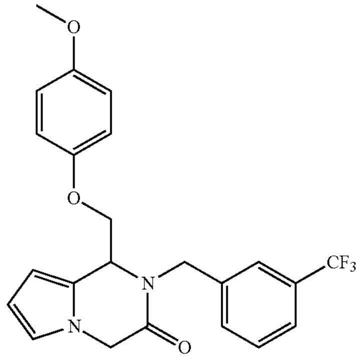

-continued
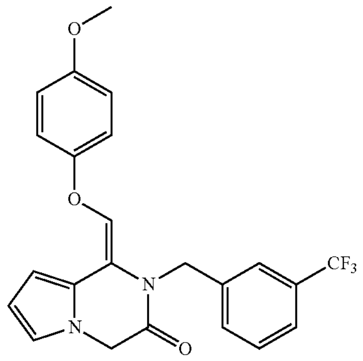
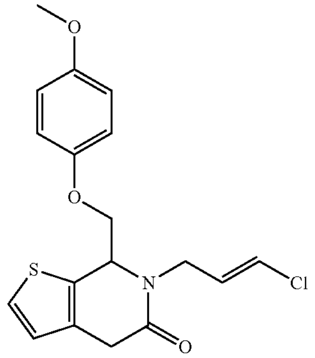
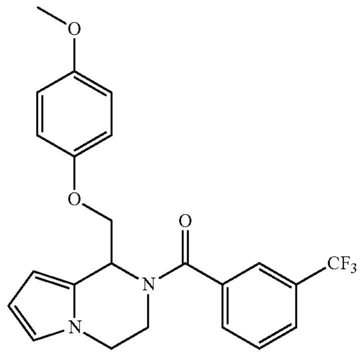
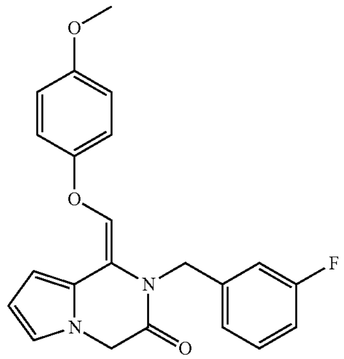
-continued
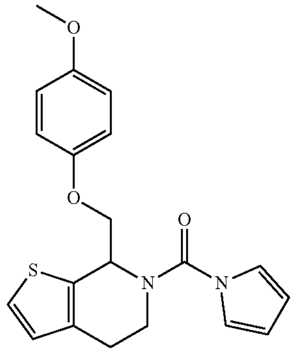
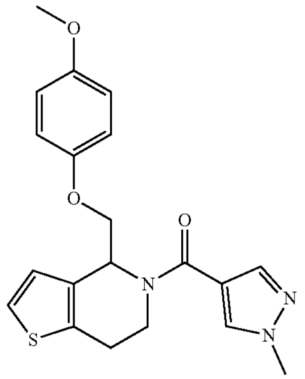
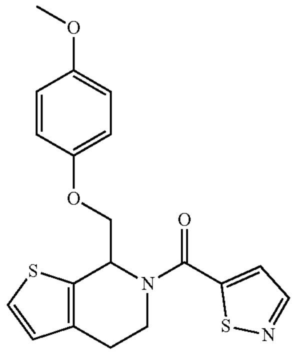
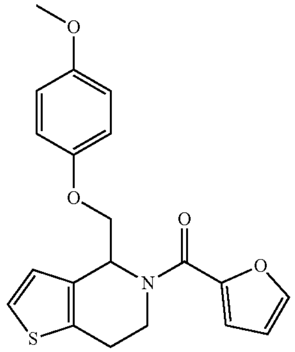

-continued
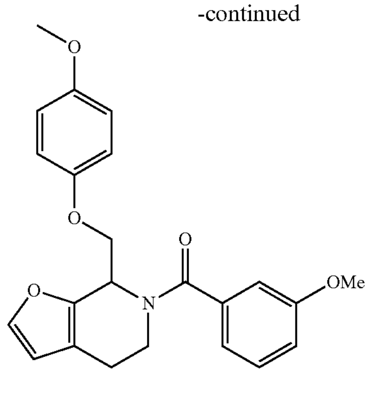
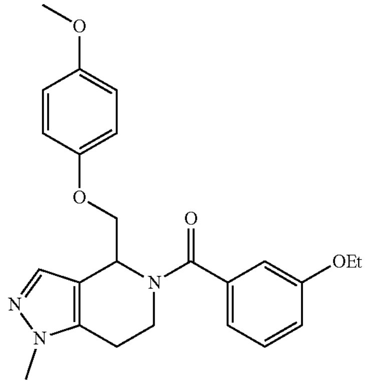
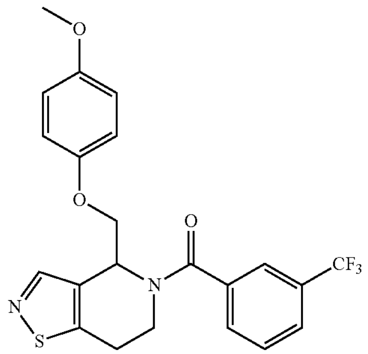
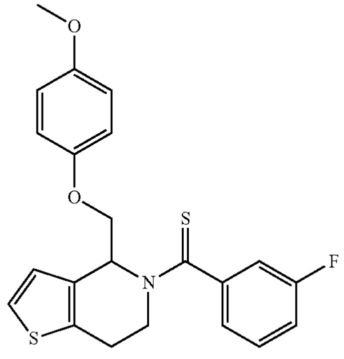
-continued
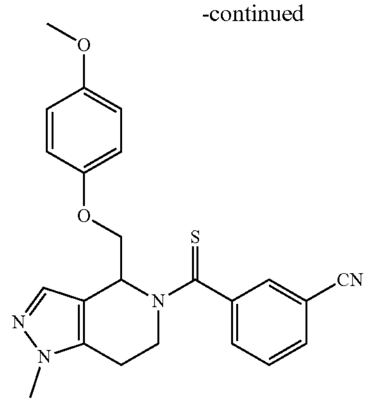
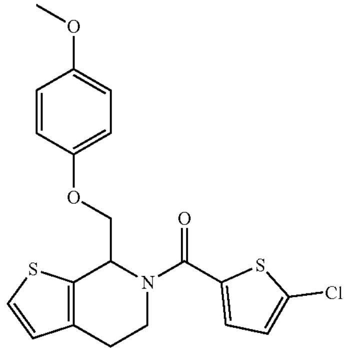
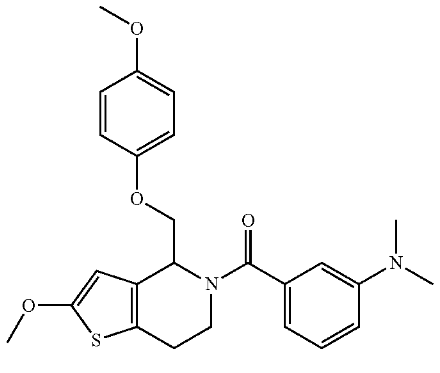
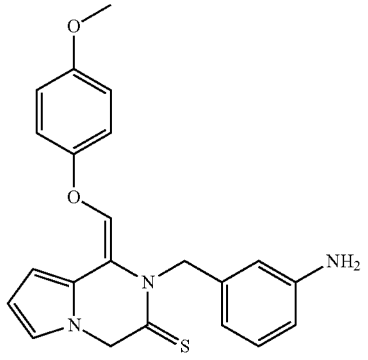

-continued
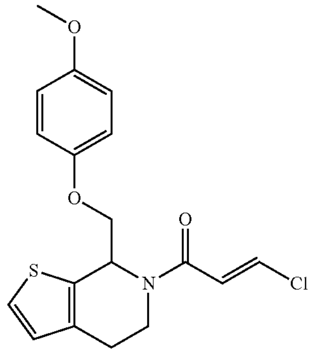
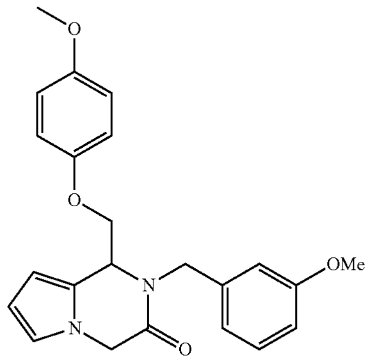
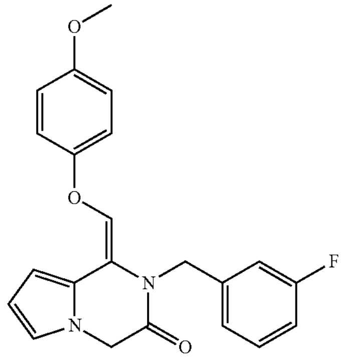
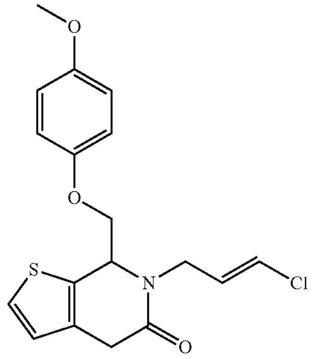
-continued
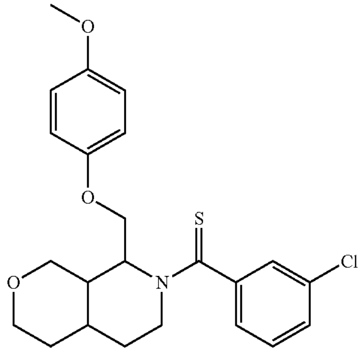
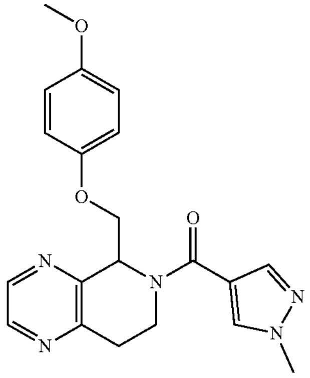
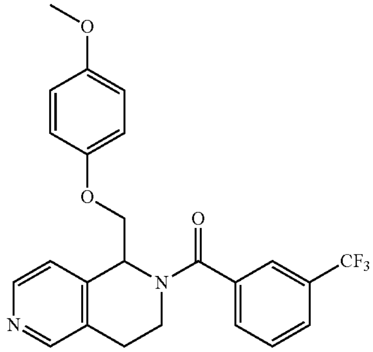
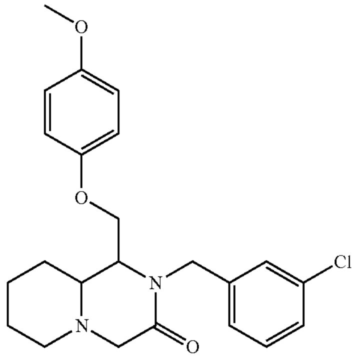

-continued

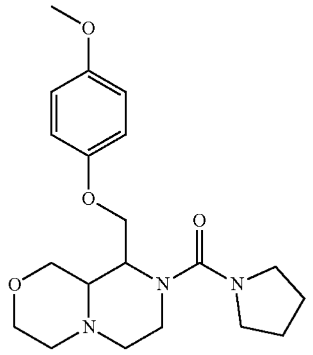

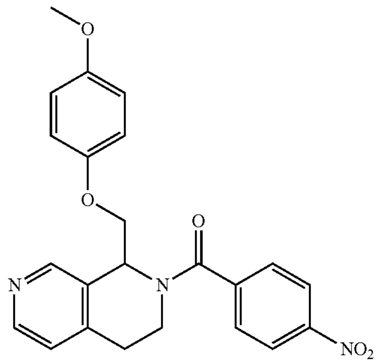

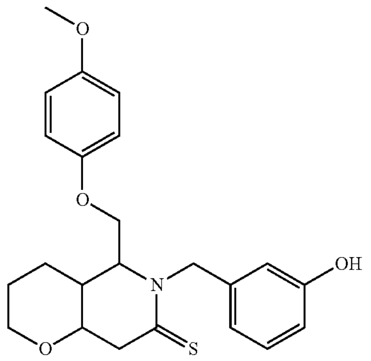

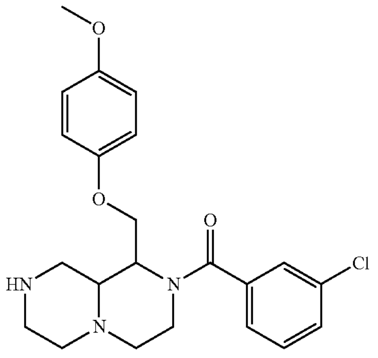

-continued

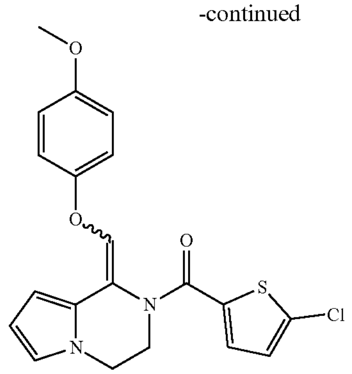

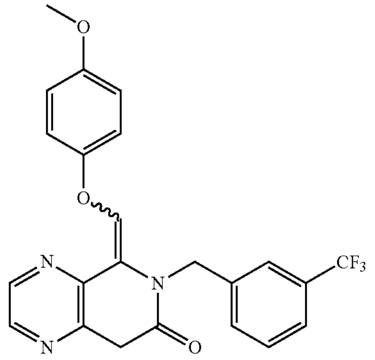

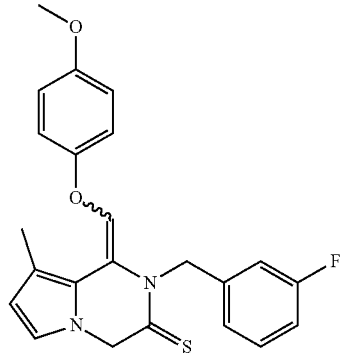

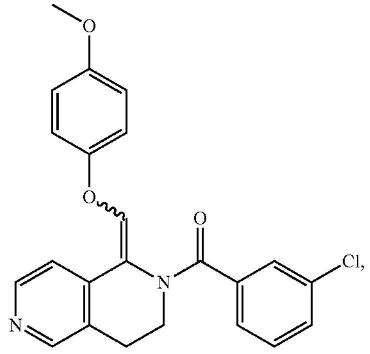

and pharmaceutically acceptable salts thereof.

2. A pharmaceutical composition comprising a compound of claim 1 and a pharmaceutically acceptable excipient.

3. The pharmaceutical composition as claimed in claim 2, which is in the form of tablet, capsule, pill, gel, granule, aerosol, aqueous buffer, nanoparticle formulation, emulsion, or liposome.

4. The pharmaceutical composition as claimed in claim 2, which comprises one or more further active agents.

5. A method of treating a neurological disorder comprising administering an effective amount of a compound of claim 1 to a subject in need thereof, wherein the neurological disorder is Alzheimer's disease, Parkinson's disease, schizophrenia, depression, stroke, or psychosis.

6. A method of treating a neurological disorder comprising administering an effective amount of a compound of claim 1 to a subject in need thereof, wherein the neurological disorder is autism, encephalitis, or age-related memory loss.

7. A method of treating a neurological disorder comprising administering an effective amount of a compound of claim 1 to a subject in need thereof, wherein the neurological disorder is ischemic injury.

8. The method of claim 7, wherein the ischemic injury is stroke, vasospasm after subarachnoid hemorrhage, traumatic brain injury, cognitive deficit after bypass surgery, cognitive deficit after carotid angioplasty, or neonatal ischemia following hypothermic circulatory arrest.

9. A method of treating a neurological disorder comprising administering an effective amount of a compound of claim 1 to a subject in need thereof, wherein the neurological disorder is sleep disorder.

* * * * *